(12) United States Patent
Martosella et al.

(10) Patent No.: US 7,943,046 B2
(45) Date of Patent: May 17, 2011

(54) METHODS AND SYSTEMS FOR ON-COLUMN PROTEIN DELIPIDATION

(75) Inventors: James D. Martosella, West Chester, PA (US); Nina I. Zolotarjova, Wilmington, DE (US)

(73) Assignee: Agilent Technologies, Inc, Santa Clara, CA (US)

( * ) Notice: Subject to any disclaimer, the term of this patent is extended or adjusted under 35 U.S.C. 154(b) by 1305 days.

(21) Appl. No.: 11/472,725

(22) Filed: Jun. 22, 2006

(65) Prior Publication Data

US 2006/0240633 A1   Oct. 26, 2006

Related U.S. Application Data

(63) Continuation-in-part of application No. 11/404,295, filed on Apr. 14, 2006, now Pat. No. 7,396,468, which is a continuation-in-part of application No. 11/055,260, filed on Feb. 8, 2005, now Pat. No. 7,449,116.

(60) Provisional application No. 60/615,176, filed on Oct. 1, 2004.

(51) Int. Cl.
B01D 15/08 (2006.01)

(52) U.S. Cl. ............ 210/635; 210/656; 210/198.2; 210/502.1; 530/413; 530/417

(58) Field of Classification Search ............ 210/635, 210/656, 198.2, 502.1; 530/413, 417
See application file for complete search history.

(56) References Cited

U.S. PATENT DOCUMENTS

| | | |
|---|---|---|
| 3,505,785 A | 4/1970 | Kirkland |
| 4,070,283 A | 1/1978 | Kirkland |
| 4,477,492 A | 10/1984 | Bergna et al. |
| 4,847,159 A | 7/1989 | Glajch et al. |
| 4,920,152 A | 4/1990 | Regnier et al. |
| 4,929,700 A | 5/1990 | Halenbeck et al. |
| 5,108,595 A | 4/1992 | Kirkland et al. |
| 5,439,829 A | 8/1995 | Anderson et al. |
| 5,731,166 A | 3/1998 | Geczy et al. |
| 5,885,921 A | 3/1999 | Krupey |
| 5,990,284 A | 11/1999 | Mahiou et al. |
| 6,057,468 A | 5/2000 | Kirkland et al. |
| 6,071,705 A * | 6/2000 | Wands et al. ............ 435/7.1 |
| 6,265,542 B1 * | 7/2001 | Fahrner et al. ............ 530/344 |
| 6,538,126 B1 | 3/2003 | Cho et al. |
| 6,730,228 B2 | 5/2004 | Petro et al. |

(Continued)

FOREIGN PATENT DOCUMENTS

WO    02/055654    7/2002

(Continued)

OTHER PUBLICATIONS

Bidlingmeyer, B. et al., "High Velocity Chromatography of Biomacromolecules", Copyright 2001.

(Continued)

*Primary Examiner* — Ernest G Therkorn

(57) ABSTRACT

Embodiments of the present invention provide a method of chromatographic delipidation comprising separating a lipid-containing sample on a superficially porous stationary phase at greater than about 70° C., at least about 80° C., having at least one mobile phase comprising an ion-pairing agent in water, an ion-pairing agent in an organic modifier, an acid in an organic modifier, and an alcohol. The invention provides minimal protein losses and high run-to-run reproducibility. The on-column delipidation method aventageously utilize reversed phase liquid chromatography.

25 Claims, 8 Drawing Sheets

U.S. PATENT DOCUMENTS

| | | | |
|---|---|---|---|
| 6,829,539 B2 | 12/2004 | Goodlett et al. | |
| 6,866,782 B2 | 3/2005 | Scapol et al. | |
| 7,323,553 B2* | 1/2008 | Fahrner et al. | 530/412 |
| 7,396,468 B2* | 7/2008 | Boyes et al. | 210/635 |
| 7,449,116 B2* | 11/2008 | Martosella et al. | 210/635 |
| 2002/0168682 A1* | 11/2002 | Goodlett et al. | 435/7.1 |
| 2003/0027354 A1 | 2/2003 | Geli | |
| 2004/0115725 A1 | 6/2004 | Pieper et al. | |
| 2004/0200776 A1 | 10/2004 | Ivanov et al. | |
| 2006/0128665 A1* | 6/2006 | Leigh et al. | 514/78 |

FOREIGN PATENT DOCUMENTS

| | | |
|---|---|---|
| WO | 2004/035169 | 4/2004 |

OTHER PUBLICATIONS

Chernokalskaya, E. et al., "Ultrafiltration for proteomic sample separation", Millpore Corporation, Life Science Division, Danvers, MA USA, Electrophoresis 2004, vol. 25, pp. 2461-2468.

Eichacker, L.A. et al., Hiding behind Hydrophobicity Department fur Biologie I, Ludwig=Masimilians Universitat Muchen, Muchen, Germany and Hoffmann-La Roche, Roche Centre for Medical Geomics, Basel, Switzerland, Journal of Biological Chemistry © 2004 by the American Society of Biochemistry and Molecular Biology, Inc., vol. 279, No. 49, Issue of Dec. 3, pp. 50915-50922, 2004.

Elortza, F. et al., "Proteomic Analysis of Glycvosylphosphatidylinositol-anchored Membrane Proteins", The American Society for Biochemistry and Molecular Biology, Inc. © 2003; Molecular & Cellular Proteomics, vol. 2, No. 12, pp. 1261-1270.

Girogion Righetti, P. et al., "Prefractionation techniques in proteoma analysis", Proteomics, 2003, vol. 3, pp. 1397-1407.

Han, J. et al., Proteolysis and Mass Spectrometic Analysis of an Integral Membrane: Aquaporin O, Department of Cell and Molecular Pharmacology, Medical Univerisity of South Carolina, Charleston, SC, Journal of Proteome Research, 2004, vol. 3, pp. 807-812, © 2004 American Chemical Society, published on the web May 19, 2004.

Lescuyer, P. et al., "Comprehensive proteome analysis by chromatographic protein prefractionation", Electrophoresis, 2004, vol. 25, No. 7-8, pp. 1125-1135, WILEY-VCH Verlag GmbH & Co. KGaA, Weinheim.

Liu, H. et al., "A Model for Random Sampling and Estimation of Relative Protein Abundance in Shotgun Proteomics", Analytical Chemistry, vol. 76, No. 14, Jul. 15, 2004, pp. 4193-4201.

Martosella, J. et al., "Optimization of Reversed-Phase Separations of Human Serum Proteins and Use in Protein Identification Human Serum Proteins and Use in Protein Identification", Agilent Technologies, Wilmington, DE 19808; ASMS 2004, ThPF483.

Martosella, J. et al., "Reversed-Phase High-Performance Liquid Chromatographic Prefractionation of Humanidepleted Human Serum Proteins to Enhance Mass Spectrometry Identification of Lower-Abundant Proteins", Agilent Technologies, Wilmington, DE 19808, Journal of Proteome Research 2005, No. 4, pp. 1522-1537, published Aug. 4, 2005.

Neverova, I, et al., "Application of reversed phase high performance liquid chromatography for subproteomic analysis of cardiac muscle", Proteomics, 2002, vol. 2, No. 1, pp. 22-31, WILEY-VCH Verland GmbH, 69451 Weinheim, 2002.

Nuhse, T. et al., Large-scale Analysis of in Vivo Phosphorylated Membrane Proteins by Immobilized Metal Ion Affinity Chromatography and Mass Spectrometry, © 2003 by The American Society for Biochemistry and Molecular Biology, Inc., Molecular & Cellular Proteomics, vol. 2, No. 11, pp. 1234-1243.

Poster, P. 1020, HPLC 2004, Philadelphia, PA, Wed-Jun. 16, 2004, "Reversed-phase high-performance liquid chromatography prefractionation prior to two-dimensional difference gel electrophoresis and mass spectrometry identifies new differentially expressed proteins, between striate cortex of kitten and adult cat", Electrophoesis 2003, vol. 24, pp. 1471-1481, 2003, WILEY-VCH Verland GmbH, 69451 Weinheim.

Ricker, R. et al., "A family of superficially porous particle HPLC columns for versatility in the rapid analysis of proteins and polypeptides at low and high pH", HPLC 2004, Philadelphia, PA, Wed-Jun. 16, 2004, Poster P-1020.

Ricker, R. et al., "High velocity chromatography A new technique for macromolecule separation", Life Science and Chemical Analysis Group, Talk #763, Presented at Pittcon, Mar. 17-21, 2002, New Orleans, LA, USA.

Ricker, R., Comparison of ZORBAX Poroshell 300Extend-C18 and Totally Porous Packing in Achieving Very Rapid, High-pH Separation of Peptides, Biotechnology/QA/QC/Basic R&D, Agilent Technologies, Inc., 2004, Printed in the USA, Feb. 20, 2004.

Woodward, C. et al., "Fast Separation of Large and Heterogeneous Proteins Using ZORBAX Poroshell C18, C8 and C3 Phases", Agilent Technologies, Inc., 2003, Printed in USA, Oct. 17, 2003.

Hage, D., "Affinity Chromatography: A Review of Clinical Applications," Clinical Chemistry 45:5, pp. 593-615 (1999).

Hage, D., "Survey of recent advances in analytical applications of immunoaffinity chromatography," Journal of Chromatography B, 715, pp. 3-28 (1998).

Huang Jun-Xiong et al., "Applications of Preparative High-Performance Liquid Chromatography to the Separation and Purification of Peptides and Proteins," Journal of Chromatography, 492, pp. 431-469 (1989).

Communication dated Nov. 23, 2006 enclosing the EP Search Report for EP Application No. 05255933.3 dated Nov. 9, 2006, and Annex to the EP Search Report, 4 pp.—Counterpart of U.S. Appl. No. 11/055,260.

Albouz-Abo, S., et al., A conformational study of the human and rat encephalitogenic myelin oligodendrocyte glycoprotein peptides 33-35, Eur. J. Biochem., 246, 59-70 (1997).

Becher, A., et al., Ectopically expressed—aminobutyric acid receptor B is functionally down-regulated in isolated lipid raft-enriched membranes, Biochemical and Biophysical Research Communications, 321, 981-987 (2004).

Becher, A., et al., The—aminobutyric acid receptor B, but not the metabotropic glutamate receptor type-1, associates with lipid rafts in the rat cerebellum, Journal of Neurochemistry, 79, 787-795 (2001).

Biel, M., et al., Tissue-specific expression of high-voltage-activated dihydropyridine-sensitive L-type calcium channels, Eur. J. Biochem, 200, 81-88 (1991).

Bledi, Y., et al., Proceed: A proteomic method for analysing plasma membrane proteins in living mammalian cells, Briefings in Functional Genomics & Proteomics, 2, 3, Research Library (Oct. 2003).

Blonder, J., et al., Enrichment of Integral Membrane Proteins for Proteomic Analysis Using Liquid Chromatography-Tandem Mass Spectrometry, Journal of Proteome Research, 1, 351-360 (2002).

Foster, L., et al., Unbiased quantitative proteomics of lipid rafts reveals high specificity for signaling factors, Proceedings of the National Academy of Sciences of the United States of America, vol. 100, No. 10, 5813-5818, May 13, 2003.

Galmarini, C., et al., Multidrug resistance in cancer therapy: Role of the microenvironment, Current Opinion in Investigational Drugs 4(12), 1418-1421 (2003).

Goshe, M., et al., Affinity Labeling of Highly Hydrophobic Integral Membrane Proteins for Proteome-Wide Analysis, Journal of Proteome Research, 2, 153-161 (2003).

Griffiths, W.J., Tandem Mass Spectrometry in the Study of Fatty Acids, Bile Acids and Steriods, Mass Spectrometry Reviews, 22, 81-152 (2003).

Heukeshoven, J., et al., Reversed-Phase High-Performance Liquid Chromatography of Virus Proteins and Other Large Hydrophobic Proteins in Formic Acid Containing Solvents, Journal of Chromatography, 252, 241-254 (1982).

Hsu, F., et al., Electrospray Ionization/Tandem Quadrupole Mass Spectrometric Studies on Phosphatidylcholines: The Fragmentation Processes, J. Am. Soc. Mass Spectrom, 14, 352-363 (2003).

Isaac, G., et al., Analysis of phosphatidylcholine and sphingomyelin molecular species frombrain extracts using capillary liquid chromatography electrospray ionization mass spectrometry, Journal of Neuroscience Methods, 128, 111-119 (2003).

Josic, D., et al., Use of selective extraction and fast chromatographic separation combined with electrophoretic methods for mapping of membrane proteins, Electrophoresis, 26, 2809-2822 (2005).

Karsan, A., et al., Proteomic Analysis of Lipid Microdomains from Lipopolysaccharide-Activated Human Endothelial Cells, Journal of Proteome Research, 4, 3490357 (2005).

Maine, S., et al., Measles Virus Structural Components Are Enriched into Lipid Raft Microdomains: a Potential Cellular Location for Virus Assembly, Journal of Virology, 305-311, Jan. 2000.

Martosella, J., et al., Reversed-Phase High-Performance Liquid Chromatographic Prefraction of Immunodepleted Human Serum Proteins to Enhance Mass Spectrometry Identification of Lower-Abundant Proteins, Journal of Proteome Research, 4, 1522-1537 (2005).

Mastro, R., et al., Protein Delipidation and Precipitation by Tri-n-butylphosphate, Acetone, and Methanol Treatment for Isoelectric Focusing and Two-Dimensional Gel Electrophoresis, Analytical Biochemestry, 273, 313-315 (1999).

McDonald, W.H., et al., Comparison of three directly coupled HPLC MS/MS strategies for identification of proteins from complex mixtures: single-dimension LC-MS/MS, 2-phase MudPIT, and 3-phase MudPIT, International Journal of Mass Spectrometry, 219, 245-251 (2002).

Meza, J.E., et al., Improved Tryptic Digestion of Proteins Using 2,2,2-Trifluoroethanol (TFE), Agilent Technologies, Poster-ABRF 2004.

Mikol, D., et al., A Phosphatidylinositol-linked Peanut Agglutinin-binding Glycoprotein in Central Nervous System Myelin and on Oligodendrocytes, The Journal of Cell Biology, vol. 106, 1273-1279, Apr. 1988.

Nebl, T., et al., Proteomic Analysis of a Detergent-resistant Membrane Skeleton form Neutrophil Plasma Membranes, The Journal of Biological Chemistry, vol. 277, No. 45, Issue of Nov. 8, 2002, pp. 43399-43409.

Oh, P., et al., Segregation of Heterotrimeric G Proteins in Cell Surface Microdomains, Molecular Biology of the Cell, vol. 12, 685-698, Mar. 2001.

Oh-Ishi, M., et al., Separation techniques for high-molecular-mass proteins, Journal of Chromatography, B, 771, 49-66 (2002).

Pike, L., Lipid rafts: bringing order to chaos, Journal of Lipid Research vol. 44, 655-667 (2003).

Pike, L., Lipid rafts: heterogeneity on the high seas, Biochem, J., 378, 281-292 (2004).

Rahbar, A., et al., Unbiased Examination of Changes in Plasma Membrane Proteins in Drug Resistant Cancer Cells, Journal of Proteome Research, 4, 2148-2153 (2005).

Riddell, D., et al., Compartmentalization of-secretase (Asp2) into low-buoyant density, noncaveolar lipid rafts, Current Biology, 11, 1288-1293 (2001).

Schluesener, D., et al., Mapping the membrane proteome of Corynebacterium glutamicum, Proteomics, 5, 1317-1330 (2005).

Simons, K., et al., Functional rafts in cell membranes, Nature, vol. 387, 569-572, Jun. 5, 1997.

Simons, K., et al., Lipid Rafts and Signal Transduction, Nature Reviews/Molecular Cell Biology, vol. 1, 31-39, Oct. 2000.

Slaughter, N., et al., The flotillins are integral membrane proteins in lipid rafts that contain TCR-associated signaling components: implications for T-cell activation, Clinical Immunology, 108, 138-151 (2003).

Tu, X., et al., Proteome Analysis of Lipid Rafts in Jurkat Cells Characterizes a Raft Subset That Is Involved in NF-K B Activation, Journal of Proteome Research, 3, 445-454, (2004).

Welling, G., et al., Column Liquid Chromatography of Integral Membrane Proteins, Journal of Chromatography, 418, 223-243 (1987).

Whitelegge, J., et al., Proteomics of Membrane Proteins, Advances in Protein Chemistry, vol. 65, 271-307 (2003).

Whitelegge, J., Tandem mass spectrometry of integral membrane proteins for top-down proteomics, Trends in Analytical Chemistry, vol. 24, No. 7, 576-582 (2005).

Whitelegge, J., et al., Full Subunit Coverage Liquid Chromatography Electrospray Ionization Mass Spectrometry (LCMS+) of an Oligomeric Membrane Protein, Molecular & Cellular Proteomics 1.10, 816-827 (2007).

Whitelegge, J., et al., Electrospray-ionization mass spectrometry of intact intrinsic membrane proteins, Protein Science, 7, 1423-1430, Cambridge University Press, (1988).

Whitelegge, J., et al., Sequence analysis of photoaffinity-labelled peptides derived by proteolysis of photosystem-2 reaction centres from thylakoid membranes treated with [14C]azidoatrazine, Eur. J. Biochem, 207, 1077-1084 (1992).

Williams, M., et al., Structure and Functional Express of a1, 1s and Subunits of a Novel Human Neuronal Calcium Channel Subtype, Neuron, vol. 8, 71-84, Jan. 1992.

Zeeberg, B., et al., GoMiner: a resource for biological interpretation of genomic and proteomic data, Genome Biology, vol. 4, Issue 4, Article R28, R28.1-R28.8 (2003).

Lee, R.P., et al., Purification of hydrophobic integral membrane proteins from Mycoplasma hyopneumoniae by reversed-phase high-performance liquid chromatography, Journal of Chromatography, A, 737, 273-279 (1996).

A.R. Castro et al., "Lipid Removal from Human Serum Samples", Clinical and Diagnostic Laboratory Immunology, Mar. 2000, vol. 7, No. 2, pp. 197-199.

* cited by examiner

| Protein | Accession Number | Score | Protein MW | # Spectra | Mean Intensity |
|---|---|---|---|---|---|
| Microsomal glutathione S-transferase 3 | O14880 | 24.07 | 16516.4 | 2 | 58100000 |
| Flotillin-1 | O75955 | 46.33 | 47355.5 | 4 | 19600000 |
| Protein C8orf2 | O94905 | 20.4 | 37839.8 | 2 | 26800000 |
| Thy-1 membrane glycoprotein precursor | P04216 | 54.56 | 17934.8 | 61 | 1150000000 |
| Sodium/potassium-transporting ATPase beta-1 chain | P05026 | 71.81 | 35061.5 | 10 | 426000000 |
| Dihydrolipoyl dehydrogenase, mitochondrial precursor | P09622 | 31.15 | 54150.5 | 2 | 90100000 |
| Cytochrome c oxidase polypeptide VIc precursor | P09669 | 26.54 | 8781.5 | 13 | 303000000 |
| ADP,ATP carrier protein, heart/skeletal muscle isoform T1 | P12235 | 39.76 | 32933.5 | 3 | 16800000 |
| Cytochrome c oxidase subunit IV isoform 1, mitochondrial precursor | P13073 | 114.67 | 19576.8 | 66 | 77100000 |
| Neural cell adhesion molecule 1, 120 kDa isoform precursor | P13592 | 24.62 | 83770.5 | 2 | 53000000 |
| Neural-cadherin precursor | P19022 | 21.63 | 99851.9 | 2 | 8740000 |
| Vacuolar ATP synthase subunit B, brain isoform | P21281 | 355.35 | 56501 | 118 | 166000000 |
| Vacuolar ATP synthase subunit C | P21283 | 161.39 | 43941.8 | 23 | 263000000 |
| Voltage-dependent anion-selective channel protein 1 | P21796 | 207.7 | 30641.5 | 103 | 51100000 |
| Oligodendrocyte-myelin glycoprotein precursor | P23515 | 49.85 | 49608.2 | 4 | 146000000 |
| ATP synthase B chain, mitochondrial precursor | P24539 | 81.95 | 28908.8 | 12 | 139000000 |
| ATP synthase alpha chain, mitochondrial precursor | P25705 | 182.46 | 59750.9 | 14 | 131000000 |
| Prohibitin | P35232 | 41.63 | 29804.2 | 4 | 14200000 |
| ATP synthase gamma chain, mitochondrial precursor | P36542 | 17.39 | 32996.2 | 2 | 37900000 |
| Vacuolar ATP synthase subunit E | P36543 | 203.63 | 26145.5 | 85 | 171000000 |
| Vacuolar ATP synthase catalytic subunit A, ubiquitous isoform | P38606 | 17.58 | 68304.5 | 2 | 46900000 |
| Voltage-dependent anion-selective channel protein 2 | P45880 | 42.79 | 38092.9 | 8 | 37300000 |
| Dihydropyridine-sensitive L-type, calcium channel subunits precursor | P54289 | 47.68 | 123184 | 4 | 34000000 |
| Vacuolar ATP synthase subunit d | P61421 | 46.33 | 40329.3 | 3 | 99100000 |
| Contactin associated protein 1 precursor | P78357 | 318.22 | 156267.5 | 42 | 152000000 |
| Contactin 2 precursor | Q02246 | 46.22 | 113393.9 | 4 | 118000000 |
| Mitochondrial 2-oxoglutarate/malate carrier protein (OGCP) | Q02978 | 25.01 | 33930.7 | 2 | 28900000 |
| Opioid binding protein/cell adhesion molecule precursor (OBCAM) | Q14982 | 30.8 | 38007.8 | 4 | 74600000 |
| Myelin-oligodendrocyte glycoprotein precursor | Q16653 | 54.63 | 28179.2 | 8 | 28500000 |
| Homer protein homolog 1 | Q86YM7 | 84.34 | 40277 | 6 | 72500000 |
| Vacuolar proton translocating ATPase 116 kDa subunit a isoform 1 | Q93050 | 46.42 | 96413.3 | 5 | 28500000 |
| Toll-interacting protein | Q9H0E2 | 25.85 | 30282 | 2 | 18800000 |
| Pleckstrin homology domain-containing protein family B member 1 | Q9UF11 | 27.3 | 27186.1 | 2 | 16600000 |
| Bassoon protein (Zinc-finger protein 231) | Q9UPA5 | 26.43 | 416370.1 | 2 | 24100000 |
| Vacuolar ATP synthase subunit D | Q9Y5K8 | 148.31 | 28263 | 24 | 105000000 |

Figure 4

METHODS AND SYSTEMS FOR ON-COLUMN PROTEIN DELIPIDATION

REFERENCE TO RELATED APPLICATIONS

This application is a Continuation-in-Part of U.S. patent application Ser. No. 11/404,295, filed 14 Apr. 2006 now U.S. Pat. No. 7,396,468, which is a Continuation-in-Part of U.S. patent application Ser. No. 11/055,260, filed 8 Feb. 2005 now U.S. Pat. No. 7,449,116, which claims priority to U.S. Provisional Application No. 60/615,176, filed 1 Oct. 2004, which is herein incorporated by reference in its entirety.

FIELD OF THE INVENTION

The present invention relates generally to chromatography, and more specifically to delipidation.

BACKGROUND

Chromatography, for example liquid chromatography (LC), gas chromatography (GC) or supercritical fluid chromatography (SFC), is employed in both analytical and preparative methods to separate one or more species, e.g., chemical compounds, present in a carrier phase from the remaining species in the carrier phase. Chromatography is also employed, in a manner independent of separation of chemical species, as a method for analyzing purity of a chemical specie, and/or as a means of characterizing a single chemical specie. Characterization of a chemical specie may comprise data, for example, a retention time for a particular chemical compound, when it is eluted through a particular chromatography column using specified conditions, e.g., carrier phase composition, flow rate, temperature, etc. These instruments may generally comprise a reservoir of mobile phase (which may be a gas, a liquid or supercritical fluid), a pump, an injector, a separation column, and a detector.

Compounds are separated by injecting an aliquot of the sample mixture into the column. The different components of the mixture pass through the separation column at different rates due to differences in their respective mobilities between the mobile phase and the stationary phase. For example, a component which is quite soluble in the stationary phase will take longer to travel through it than a component which is not very soluble in the stationary phase but very soluble in the mobile phase. As a result of these mobility differences, sample components are separated from each other as they travel through the stationary phase. The instrument may then elute the solutes to a flow-through detector, such as a mass spectrometer. The solutes may, alternatively, pass to a collection system for later use, further analysis, or successive separation.

For reversed phase liquid chromatography systems, the mobile phase typically comprises water and one or more water-miscible organic modifiers, for example, acetonitrile or methanol. The specie-of-interest typically forms a solution with the mobile phase. Affinity of a specie for a stationary phase, which affects the rate at which a particular specie in a carrier phase passes through a stationary phase, results primarily from interaction of the specie with chemical groups present on the stationary phase. Chemical groups may be provided on the stationary phase by reacting a surface-modifying reagent with a substrate, such as a silica substrate. Surface-modifying agents may thus be employed to adsorb specific chemical groups onto the stationary phase. There is a continuing need in the art for improved chromatographic methods for the separation of eluent species.

Processing of biological materials may involve the use of liquid chromatography to separate and harvest cellular product or metabolite of interest from cellular debris or cell media. The separated biological components may be collected post-separation and thus fractionated for purposes ranging from protein purification or sample reduction prior to other downstream analyses. Generally, the eluent may be monitored using an ultraviolet-visible (UV-VIS) light-range spectrophotometer, and fractions which are thought to contain the product of interest are collected and sometimes pooled. The fractions may be further analyzed using any of a variety of biochemical analyses, such as Western blotting, SDS-PAGE, ELISAs, protein sequencing, or the like, in order to determine the presence of the target analyte(s), quantify the identified analyte(s), or both.

Some of the most important cellular functions, including cell signaling, are implicated in a number of proteins tied to biological membranes, e.g., lipid rafts. Lipid rafts, also referred to as detergent resistant membrane fragments, are localized cell membrane regions, or subdomains, enriched in cholesterol, glycosphingolipids, and integral membrane proteins. See e.g., Foster et al., *Proc. Natl. Acad. Sci. USA* 100 (10):5813-8 (2003); also Simons et al., *Nat. Rev. Mol. Cell Biol.* 1(1):31-9 (2000). These heterogeneous membrane fragments were originally associated with lipid trafficking, but now appear to be implicated in a variety of biological processes, such as signal transduction, endocytosis, protein processing and pathogen entry. See e.g., Becher et al., *Biochem. Biophys. Res. Commun.* 321(4):981-7 (2004); also Manie et al., *J. Virol.* 74(1):305-11 (2000). However, proteomic samples, such as human serum, or lipid rafts are particularly complex and challenging to isolate and separate due to the large range of protein concentrations. Moreover, lipids present in biological extracts may bind to proteins and interfere with protein detection, quantization, or both. As a result, membrane proteins are generally less studied than soluble proteins due to the numerous impediments encountered in the delipidation, protein separation and structure/function analyses of this protein class.

Lipid rafts, nonetheless, are a readily accessible source of membranous material enriched in integral membrane proteins, and as such, provide a good starting material to define separations conditions that have broad utility. Lipid rafts are commonly prepared from cultured cells and disrupted tissues by selective solubilization with detergents, followed by differential centrifugation. Significant dependencies on protein and lipid compositions of such preparations are seen, based on the conditions used for detergent extraction and sample workup. See e.g., Pike, *J. Biochem. J.* 378 (Pt 2):281-92 (2004).

Traditionally, proteomic analyses of complex protein samples involve the resolution of proteins using two-dimensional gel electrophoresis (2DGE), followed by the identification of resolved proteins by mass spectrometry or simply by shotgun proteomics methods, which combine two dimensional LC and mass spectrometry. However, by either method, solubility and recovery of proteins remains an obstacle. For 2D gel electrophoresis, many hydrophobic proteins are not solubilized in the non-detergent isoelectric focusing sample buffer and solubilized proteins are prone to precipitation at their isoelectric point. For shotgun proteomic methods, as well as 2DGE, limited dynamic range of detection is also at issue because membrane proteins are typically lower in abundance when compared with soluble proteins. To resolve this problem, lipids are often solubilized using detergents in order to delipidate the associated proteins. However, certain chromatographic methods, such as reversed phase- HPLC (RP-HPLC), poorly tolerate the presence of detergent in samples, and become all but inoperable with the addition of detergent to the mobile phase. In fact, RP-HPLC separations of complex protein samples generally have low sample recoveries, and provide poor reproducibility and inadequate resolution. Consequently, chromatography of high-molecular-mass hydrophobic proteins presents a myriad of challenges that often prohibit their utility and impede investigation.

Alternatively, samples may be delipidated using an organic modifier or a mixture of organic modifiers. For example, a common delipidating procedure for plasma, protein solutions, cell culture, or disrupted tissue involves the use of a mixture of butanol and di-isopropyl ether or acetone or ethanol precipitation. Using these methods, the proteins precipitate while the organic phase retains the dissolved lipids. Many of these methods also generally require further centrifugation and extraction steps. Still further, these typical dilapidation methods generally exhibit several failings including protein losses, and solubility or miscibility concerns, making it difficult to fully recover proteins or lipids of interest. Indeed, protein losses and method reproducibility, remain a significant problem in the art.

Considerable research has, therefore, been directed toward the development of chromatographic delipidation methods suitable for protein-containing mixtures, such as biological fluids. For example, U.S. Pat. No. 5,885,921 discloses hydrophobic silica that may be suitable for the adsorption of lipids from whole blood. As stated in the '591 patent, however, such a product is not suitable as a chromatographic support media. Thus, there remains a need in the art for delipidation methods, including on-column methods, suitable for use with lipid-containing mixtures having high lipid content and/or high protein content. Further, there exists a need for on-column delipidation techniques that minimizes protein losses and/or improves sample processing and reproducibility.

SUMMARY OF THE INVENTION

Presently preferred embodiments of the present invention provide direct, on-column chromatographic delipidation methods. In certain embodiments, the chromatographic delipidation methods provide minimal protein losses while providing high run-to-run reproducibility and robust sample processing. In yet other embodiments, the delipidation method may also simultaneously provide sample de-salting, protein fractionation, or both. Still further, the lipid fraction(s), protein fraction(s), or both may be collected by an automated fraction collector for further chromatographic separation or analysis.

Accordingly, certain presently preferred aspects of the invention provide a method of chromatographic delipidation comprising separating a chromatographic sample on a silica-based stationary phase, preferably an at least partially superficially porous stationary phase, at greater than about 70° C. and at least one mobile phase comprising an ion-pairing agent in water, an ion pairing agent in an organic modifier, an acid in an organic modifier, an alcohol, or combinations thereof. In certain aspects of the invention the temperature may be at least about 80° C. In yet other aspects of the invention, singly or in combination, the ion pairing agent may comprise trifluoroacetic acid (TFA), the organic modifier may comprise acetonitrile (ACN), the acid may comprise formic acid, and the alcohol may comprise isopropanol. The method may comprise reversed phase high performance liquid chromatography (RP-HPLC).

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

FIG. 4 depicts 35 human brain lipid raft-associated integral membrane protein identifications from 48 1D SDS-PAGE bands.

DETAILED DESCRIPTION OF CERTAIN PREFERRED EMBODIMENTS

Figure 1:
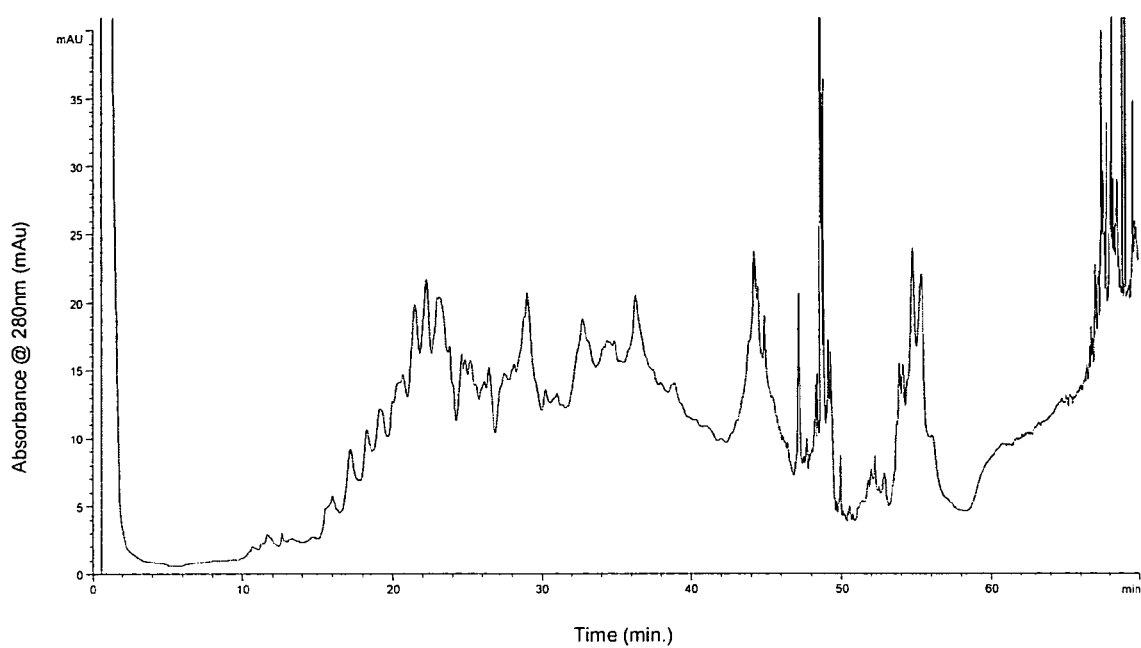
FIG. 1 depicts a representative chromatogram depicting RP delipidation of human brain lipid rafts on a 4.6-mm×50-mm mRP-C18 column.

Certain aspects of the invention provide a method of chromatographic delipidation comprising separating a lipid-containing sample on a silica-based stationary phase at greater than about 70° C., at least about 80° C. In certain embodiments the silica-based stationary phase may be, at least partially, superficially porous. The method may further comprise at least one mobile phase comprising an ion-pairing agent in water, an ion pairing agent in an organic modifier, an acid in an organic modifier, an alcohol, or combinations thereof. In yet other aspects of the invention, the ion pairing agent may comprise trifluoroacetic acid (TFA), the organic modifier may comprise acetonitrile (ACN), the acid may comprise formic acid, and the alcohol may comprise isopropanol, singly or in combination. In certain embodiments, the method may be performed as part of reversed phase high performance liquid chromatography (RP-HPLC). Still further, fractionating the sample may reduce sample complexity and can facilitate improved downstream analysis. As used herein, "delipidation" refers to partially, or completely, chromatographically separating a sample, such as a protein-containing mixture, into its component lipid and protein constituents.

During the past decade, there have been many advances in understanding lipid modifications of proteins, spanning not only enzymology and biochemistry, but also genetic and pharmacologic studies linking lipid modifications to the pathogenesis and treatment of human disease. All eukaryotic cells contain elaborate systems of internal membranes comprising proteins and lipids, which set up various membrane-enclosed compartments within the cell. Lipids are a class of hydrocarbon-containing organic compounds essential for the structure and function of living cells. The lipid fraction varies considerably, ranging from, e.g., myelin contains only 18% protein and 76% lipid, to mitochondrial inner membrane containing 76% protein and only 24% lipid, to plasma membranes of human red blood cells and mouse liver contain nearly equal amounts of proteins and lipids (44/49 percent and 43/52 percent respectively).

Lipids are generally characterized as being water-insoluble and soluble in nonpolar organic solvents, such as ether. Usually they are aliphatic, but they can have rings in their structure. The lipids in the plasma membrane are chiefly phospholipids, like phosphatidyl ethanolamine, and cholesterol, and the lipid bilayer gives the membranes its fluid characteristics. Phospholipids are amphiphilic with a pair of hydrophobic, hydrocarbon tails. Cholesterol has a rigid ring system and a short branched hydrocarbon tail. Cholesterol is largely hydrophobic, but has one hydroxyl polar group, making it amphipathic. When present, cholesterol inserts within the phospholipid molecules and prevents crystallization of hydrocarbons and phase shifts in the membrane.

Sphingolipids (particularly glycosphingolipids) in the plasma membrane outer leaflet tend to separate out from glycerophospholipids, and co-localize with cholesterol into microdomains, called "lipid rafts." Glycerophospholipids often include at least one fatty acid that is kinked, due to the presence of one or more double bonds. As previously noted, lipid rafts are also resistant to detergent solubilization. The close packing of sphingolipids in association with cholesterol has been attributed to the lack of double bonds in sphingolipid hydrocarbon chains. Proteins with covalently attached lipid anchors (fatty acid or glycosylphosphatidylinositol) tend to associate with raft domains, making separation particularly difficult.

Certain embodiments of the present invention using RP-HPLC separation may effectively resolve complex lipids and proteins, and exhibit improved tolerance of residual detergents. These embodiments are particularly suited for proteomic analyses wherein the separation methods need to be highly reproducible and demonstrate high recovery of protein or lipids, thereby avoiding the problem of introducing systematic bias for proteomic comparative studies.

The samples, such as may be used herein, comprise a "biological fluid" including, but is not limited to, blood, plasma, serum, sputum, urine, tears, saliva, sputum, cerebrospinal fluid, lavages, leukapheresis samples, milk, ductal fluid, perspiration, lymph, semen, umbilical cord fluid, and amniotic fluid, as well as fluid obtained by culturing cells, such as fermentation broth and cell culture medium. Typically, the sample is a "peptide mixture," which is typically a complex mixture of peptides. A "sample of proteins" is typically any complex mixture of proteins and/or their modified and/or processed forms, which may be obtained from sources, including, without limitation: a cell sample (e.g., lysate, suspension, collection of adherent cells on a culture plate, a scraping, a fragment or slice of tissue, a tumor, biopsy sample, an archival cell or tissue sample, laser-capture dissected cells, etc), an organism (e.g., a microorganism such as a bacteria or yeast), a subcellular fraction (e.g., comprising organelles such as nuclei or mitochondria, large protein complexes such as ribosomes or Golgi, and the like), an egg, sperm, embryo, a biological fluid, viruses, and the like "Protein", as used herein, means any protein, including, but not limited to peptides, enzymes, glycoproteins, hormones, receptors, antigens, antibodies, growth factors, etc., without limitation. Proteins include those comprised of greater than about 20 amino acids, greater than about 35 amino acid residues, or greater than about 50 amino acid residues.

In certain embodiments, a chromatographic delipidation method is provided, comprising: fractionating a sample on a superficially porous phase with a gradient composition comprised of varying amounts of an ion-pairing agent, a pH-conditioning reagent and/or organic modifier and thereafter contacting the stationary phase with a greater than about 80% organic phase (e.g., such as an organic phase comprising an organic modifier such as acetonitrile), a greater than about 85% organic phase, a greater than about 90% organic phase, a greater than about 95% organic phase or a 100% organic phase. As used herein, a superficially porous stationary phase may comprise a core of non-porous material and an outer layer of porous material. Still further, as used herein, an "organic modifier" refers to a reagent or a compound which may be used in chromatographic procedures and like separation methods, to alter the properties of the mobile phase to controllably effect serial elution of desired materials. "Separation," as used herein, refers to partially, or completely, chromatographically dividing, a substance, such as a protein mixture, into its component parts, such as similar protein molecules, and optionally the removal of impurities. Still further, as used herein, "fractionation" refers to the act of separating a sample and/or collecting samples of the eluate For example, an organic modifier may decrease ionic interactions between molecules in the mobile phase and the solid phase. In certain embodiments, an organic modifier comprises a reagent added to a mobile phase to decrease its polarity. Suitable organic modifiers include, but are not limited to, acetonitrile, ethanol, methanol, ethanol, n-propanol or isopropanol (e.g., 1- or 2-propanol).

A "membrane sample" refers to a sample of proteins including membrane components such as membrane-associated proteins and lipids (i.e., phospholipids). Membrane-associated proteins includes extrinsic or peripheral proteins and intrinsic proteins, including receptor proteins and cell adhesion proteins, as well as or including modified proteins, such as glycoproteins. A membrane sample may also include structures, such as lipid rafts and caveolae. Caveolae are invaginated lipid raft domains of the plasma membrane that have roles in cell signaling and membrane internalization. Membrane samples may also include cholesterol, fatty acids, glycoproteins, and hopanoids.

In certain embodiments, the membrane sample is a sample of complex proteins. A "sample of complex proteins" may contain greater than about 100, about 500, about 1,000, about 5,000, about 10,000, about 20,000, about 30,000, about 100,000, or more different proteins. Such samples may be derived from a natural biological source (e.g., cells, tissue, bodily fluid, soil or water sample, and the like) or may be artificially generated (e.g., by combining one or more samples of natural and/or synthetic or recombinant sources of proteins).

In at least one embodiment of the present invention, the sample comprises at least one biological sample having associated lipids and proteins. In certain embodiments, the protein fraction may comprise complex protein having greater than about 100, about 500, about 1,000, about 5,000, about 10,000, about 20,000, about 30,000, about 100,000, or more different proteins. In still further aspects, the sample comprises at least one of biological fluid(s) and membrane fragment(s). In additional aspects, after equilibration in a greater than about 80% organic phase, the stationary phase is reused to separate another sample. In one aspect, the stationary phase is reused at least about 5 times, at least about 10 times, at least about 20 times, at least about 30 times, at least about 40 times, or at least about 50 times.

In certain aspects, prior to fractionation using superficially porous phases according to the disclosure, a chromatographic sample, such as a protein-rich or membrane bound sample, is contacted with an immunoaffinity stationary phase to deplete the sample of undesired proteins, such as high abundance proteins. This also may be used to enrich the sample for one or more types of proteins or protein fragments (e.g., glycoproteins, cysteine-containing proteins, or phosphopeptides). Both immunodepletion and enrichment of a sample may be performed prior to using the superficially porous phase according to the present disclosure.

In certain other aspects, protein-rich samples are contacted with a cleaving agent, such as trypsin, to generate a peptide sample. Such contacting may be done prior to, or after, an immunoaffinity separation step, or prior to, or after separating using the superficially porous phase.

Lipids, or proteins separated using a silica-based stationary phase, preferably at least one superficially porous stationary phase may be detected and/or quantified and/or further characterized to determine their properties, such as amino acid sequence, mass/charge ratio and the like. In one aspect, separated proteins or peptides are analyzed by a proteome analysis system, such as one including a mass spectrometer. The term "proteome" refers to the protein constituents expressed by a genome, typically represented at a given point in time. A "sub-proteome" is a portion or subset of the proteome, for example, the proteins involved in a selected metabolic pathway, or a set of proteins having a common enzymatic activity. The term "proteomic analyses" refers to any number of scientific methods used to determine, or evaluate, the structure, or function, of at least one proteome.

The term "assessing" and "evaluating" and "analyzed" are used interchangeably herein to refer to any form of measurement, and includes determining if an element is present or not. The terms "determining," "measuring," and "assessing," and "assaying" and "analyzing" are used interchangeably and include both quantitative and qualitative determinations. Assessing may be relative or absolute. "Assessing the presence of" includes determining the amount of something present, as well as determining whether it is present or absent.

In certain embodiments, systems are provided for performing protein/lipid separations. In another aspect, the system comprises a separation module comprising a superficially porous phase operably interfaced with a proteomic analysis system, such as a mass spectrometer. In a further aspect, the system comprises a module for performing an immunoaffinity separation, a separation module comprising a superficially porous stationary phase and a proteomic analysis system.

As used herein, an "information management systems" may be used, referring to a program, or series of programs, which may search a database and determine relationships between data identified as a result of such a search. Components of such a system are "in communication with" or "communicates with" other components of a system, such as receiving input from that component and/or providing an output to that component to implement a system function. A component which is "in communication with" or which "communicates with" another component may be, but is not necessarily, physically connected to the other component. For example, the component may communicate information to the other component and/or receive information from the other component. "Communicating information" refers to transmitting the data representing that information as signals (e.g., electrical, optical, radio, magnetic, etc) over a suitable communication channel (e.g., a private or public network). "Input" or "Output" may be in the form of electrical signals, light, data (e.g., spectral data), materials, or may be in the form of an action taken by the system or component of the system. The term "in communication with" also encompasses a physical connection that may be direct or indirect between one system and another or one component of a system and another. "Forwarding" an item refers to any means of getting that item from one location to the next, whether by physically transporting that item or otherwise (where that is possible) and includes, at least in the case of data, physically transporting a medium carrying the data or communicating the data.

A "computer-based system" refers to the hardware means, software means, and data storage means used to analyze the information of the present disclosure. The minimum hardware of the computer-based systems of the present disclosure comprises a central processing unit (CPU), input means, output means, and data storage means. A skilled artisan may readily appreciate that any one of the currently available computer-based system are suitable for use in the present disclosure. The data storage means may comprise any manufacture comprising a recording of the present information as described above, or a memory access means that may access such a manufacture. In certain instances a computer-based system may include one or more wireless devices. Any convenient data storage structure may be chosen, to "record" data into a computer readable medium for storing information, using any such methods as known in the art a based on the means used to access the stored information. A variety of data processor programs and formats may be used for storage, e.g., word processing text file, database format, etc.

A "processor" refers to any hardware and/or software combination which will perform the functions required of it. For example, any processor herein may be a programmable digital microprocessor such as available in the form of a electronic controller, mainframe, server or personal computer (desktop or portable). When the processor is programmable, suitable programming may be communicated from a remote location to the processor, or previously saved in a computer program product (such as a portable or fixed computer readable storage medium, whether magnetic, optical or solid state device based). For example, a magnetic medium or optical disk may carry the programming, and may be read by a suitable reader communicating with each processor at its corresponding station. By "remote location," is meant communication to a location other than the location at which the affinity purification and/or mass spectroscopy occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

As used herein, a "database" is a collection of information or facts organized according to a data model, which determines whether the data is ordered using linked files, hierarchically, according to relational tables, or according to some other model determined by the system operator. An "interface on the display of a user device" or "user interface" or "graphical user interface" is a display (comprising text and/or graphical information) displayed by the screen or monitor of a user device connectable to the network which enables a user to interact with a system processor and/or system memory (e.g., including a data base and information management system). "Providing access to at least a portion of a database" refers to making information in the database available to user(s) through a visual or auditory means of communication.

In one embodiment of the invention, the system comprises a processor for providing instructions to various modules of the system to implement system functions. In one aspect, the processor provides instructions to the separation module to perform a separation at a temperature of at least about 70° C. Separation may also be performed at a temperature of at least about 80° C. In yet other aspects the temperature may be up to 95° C. In another aspect, the separation module comprises a mechanism for controlling the temperature of the separation module that is controllable by the system processor. For example, in one aspect, the separation module comprises a column comprising a heatable column jacket, responsive to instructions from the system processor.

In a further aspect, the system processor provides instructions to fluidics in communication with the separation module to contact a superficially porous stationary phase in the separation module with a gradient composition comprising varying amounts of an ion-pairing agent, a pH-conditioning reagent and/or organic modifier after selected intervals of time. In still a further aspect, the system processor provides instructions for equilibrating the separation module in an at least about 80% organic phase (such as an organic phase comprising an organic modifier, such as acetonitrile), a greater than about 85% organic phase, a greater than about 90% organic phase, a greater than about 95% organic phase or a 100% organic phase, prior to performing a new separation procedure. In one aspect, the system processor instructs the system to repeat at least about 5 separation cycles, at least about 10 separation cycles, at least about 20 separation cycles, at least about 30 separation cycles or at least about 50 separation cycles. In certain aspects, new separation modules are provided to the system (either manually or in an automated process) after at least about 5 separation cycles, at least about 10 separation cycles, at least about 20 separation cycles, at least about 30 separation cycles or at least about 50 separation cycles.

In the present invention, methods are provided for the separation and fractionation, of lipid-containing samples. In certain embodiments, RP-HPLC methods are provided for the separation and fractionation of lipid-containing samples, which may or may not first be immuno-depleted to reduce the complexity of the samples, and to remove undesired constituents (such as high abundance proteins), by binding desired proteins (e.g., cysteine-containing proteins) to an affinity matrix and recovering the bound proteins or by using a combination of the above techniques. In aspects of the invention, the superficially porous stationary phase, comprising a core of non-porous material and an outer layer of porous material, has an outer layer of porous material, comprising a chromatographically active material, such as an organosilane or modified form thereof. When applied in-column, the outer layer of porous material, in certain embodiments, comprises silica particles stably associated with the non-porous core (i.e., the particles remain associated with the core under the conditions being used for separation).

In further embodiments, the method yields separated proteins in recoveries of from about 70-100 weight percent of the mixture of proteins, or from about 95-100 weight percent of the mixture of proteins. In yet other embodiments, delipidation effectiveness is proportionally related to temperature.

Superficially Porous Stationary Phase

The superficially porous stationary phase, in certain embodiments, have particles having an average particle diameter of, for example, about 2 to about 20 micrometers, such as about 10 micrometers, and preferably have an average particle diameter of about 3 to about 5 micrometers. In certain aspects, when the stationary phases are used in RP-HPLC, the reversed phase of the porous stationary phase is a silane, in embodiments, comprising a $C_6$ to about $C_{30}$ hydrocarbon, such as an alkane, a substituted alkane, an alkene, a substituted alkene, an aryl or substituted aryl, and like hydrocarbons, or combinations thereof. Similarly, possible silane substituents of a hydrocarbon are, for example, either partially or fully substituted fluorocarbons, or contain additionally, or alternatively, other halogen atoms in positions occupied by hydrogen atoms in hydrocarbons. Additional possible substituents of a "substituted" hydrocarbon are, for example, a saturated or unsaturated, straight or branched $C_1$ to about $C_6$ hydrocarbon, a cyano, an amino, an hydroxyl, a carbamate, an amide, an urea, a succinimide, a saturated or unsaturated, straight or branched $C_1$ to about $C_6$ alkyl ether, such as an alkoxy group, an ester, an aryl, and like groups, and combinations thereof.

In various embodiments, halo includes fluoro, chloro, bromo, or iodo. Alkyl, alkoxy, etc., include straight, branched, and cyclic groups; but reference to an individual radical such as "propyl" embraces only the straight chain radical, a branched chain isomer, such as "isopropyl" being specifically referred to. "Alkyl" includes linear alkyls, branched alkyls, and cycloalkyls. "Aryl" includes a phenyl radical or an ortho-fused bicyclic carbocyclic radical having about nine to twenty ring atoms, in which at least one ring is aromatic. Aryl (Ar) may include substituted aryls, such as a phenyl radical having from 1 to 5 substituents, for example, alkyl, alkoxy, halo, and like substituents. Examples of superficially porous stationary phases are disclosed, for example, in U.S. Pat. Nos. 3,505,785, 4,070,283, and 4,477,492, the disclosures of which are incorporated by reference herein in their entirety.

Pore sizes of stationary phases used in methods according to the disclosure may vary and may be varied to suit a particular biomolecule being separated. In one aspect, the average pore size is greater than or equal to about 300 Å, while in another aspect, stationary phases having pore sizes of less than 300 Å are used.

The reversed phase of the superficially porous stationary phase may be, for example, a silane compound having a $C_6$ to about $C_{30}$ hydrocarbon group. The reversed phase of the superficially porous stationary phase may be, for example, a divalent silane having a structure:

—Si(R)(Me)-(CH$_2$)$_3$—Si(R)(Me)- wherein, for example, R is an n-octadecyl group, an n-tetradecyl group, or mixtures thereof, and Me is methyl. The terminal "—" marks represent points of attachment of the divalent silane to a surface group or stationary phase. U.S. Pat. Nos. 6,057,468 and 5,948,531, disclose bidentate silanes suitable for use in forming the bonded reversed phase of the macroporous or superficially porous phases of the present disclosure. Still further, the reversed phase of the superficially porous stationary phase may, for example, comprise a silane of the formula:

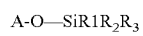
A-O—SiR1R$_2$R$_3$ wherein R$_1$, R$_2$, and R$_3$ are each independently alkane, substituted alkane, alkene, substituted alkene, aryl or substituted aryl; and A is a surface group of the substrate to which the silane is attached. In embodiments, the reversed phase are, for example, a $C_3$ to about $C_{30}$ hydrocarbon or a corresponding monovalent or bivalent silane compound having a $C_{10}$ to about $C_{30}$ hydrocarbon, such as a —SiR$_2$C$_{3\text{-}30}$ for a monovalent silane, of the formula —Si(R)(Me)-(R')—Si(R)(Me)-for a bivalent silane where R' is a divalent hydrocarbon spacer group with from 1 to about 10 carbon atoms, such as —Si(C$_{3\text{-}30}$)(Me)-(CH$_2$)$_3$—Si(C$_{3\text{-}30}$)(Me)-. In embodiments, the hydrocarbon of the reversed phase hydrocarbon or the corresponding monovalent or bivalent silanes are, for example, a substituted or unsubstituted, straight or branched, $C_3$ to $C_{20}$ hydrocarbon, such as a $C_{18}$ hydrocarbon. U.S. Pat. No. 4,847, 159 discloses substrates coated with sterically protected organo-silanes suitable for use in preparing the bonded reversed phase of the macroporous or superficially porous phases of the present disclosure.

Sample Preparation

The mixture of lipids and proteins, prior to fractionating, may be denatured, for example, in an aqueous mixture of urea and acetic acid, such as about 6 M urea and about 1 weight % aqueous acetic acid or may be solubilized in a strong acid such as, but not limited to trifluoroacetic acid (TFA), formic acid, or heptafluorobutyric acid (HFBA). The mixture of proteins may be eluted, for example, with a gradient composition comprised of varying amounts of an ion-pairing agent, a pH-conditioning reagent, and/or organic modifier.

Mobile Phase

In certain aspects, the gradient composition comprises an ion-pairing agent that binds by ionic interaction to solute molecules to increase their hydrophobicity. Suitable ion-pairing agents include, but are not limited to: anionic ion-pairing agents, such as, for example, trifluoroacetic acid (TFA), pentafluoroproprionic acid (PFPA), heptafluorobutyric acid (HFBA), and cationic ion pairing agents, such as, for example, tetramethylammonium chloride, tetrabutylammonium chloride, and triethylamine.

In another aspect, an aqueous reagent is provided which when used with an organic modifier will regulate the elution of proteins. In one aspect, the aqueous reagent comprises low pH e.g., for providing a gradient composition comprising a pH of less than about 5, less than about 4 or between about 2-4. The low pH may minimize surface silanol effects, aid in protein denaturation, and/or allow the proteins to remain soluble. Suitable low pH-conditioning reagents include, but are not limited to, formic acid, trifluoroacetic acid, heptafluorobutyric acid and ortho-phosphoric acid. Mobile phases containing ammonium acetate or phosphate salts are suitable for use at a pH closer to neutrality.

In certain aspects, the ion-pairing agent also may serve as the pH-conditioning reagent. For example, one ion-pairing agent, such as trifluoroacetic acid, may also be used to maintain a low pH of the mobile phase.

In a further aspect, the gradient composition comprises one or more organic modifiers. As used herein, an "organic modifier" refers to a reagent or a compound which may be used in chromatographic procedures to alter the properties of the mobile phase to controllably effect serial elution of desired materials. In one aspect, an organic modifier decreases ionic interactions between molecules in the mobile phase and the stationary phase. For example, in one aspect, an organic modifier comprises a reagent added to a mobile phase to decrease its polarity. Suitable organic modifiers include, but are not limited to, acetonitrile, tetrahydrofuran (THF), methylene chloride, ethanol, methanol, ethanol, n-propanol, or isopropanol (e.g., 1- or 2- propanol).

In embodiments, the gradient elution may be accomplished, for example, stepwise, linearly, with multisegmented linear or stepwise changes in composition, or with a combination thereof. In one aspect, gradient elution is performed in increasing amounts of organic modifier at elevated temperature and elution is facilitated in greater than about 10%, greater than about 20%, greater than about 30%, greater than about 90%, or up to about 100% of organic modifier. In certain aspects, lipid elution is facilitated in increasing amount of organic modifier and a strong acid.

In one aspect, the gradient composition comprises aqueous trifluoroacetic acid and acetonitrile. For example, separation may be accomplished using a mobile phase including: about 0.01 to about 2 weight % trifluoroacetic acid in water, referred to as reagent (A); 0.01 to about 2 weight % trifluoroacetic acid in acetonitrile, referred to reagent (B); and combinations or mixtures thereof. In embodiments, the mobile phase may be, for example, from about 0.01 to about 2 weight % trifluoroacetic acid in water, for example, 0.1 weight % trifluoroacetic acid in water and having increasing amounts of an organic modifier over time. In embodiments, the mobile phase may be from about 0.01 to about 2 weight % trifluoroacetic acid in water, such as 0.08 weight % aqueous trifluoroacetic acid in acetonitrile and having increasing amounts of acetonitrile over time.

In a further aspect, the gradient composition comprises aqueous trifluoroacetic acid, acetonitrile, formic acid, and isopropanol. For example, separation may be accomplished using a mobile phase including one or more of the following: (A) about 0.01 to about 2 weight % trifluoroacetic acid in water; (B) about 0.01 to about 2 weight % trifluoroacetic acid in acetonitrile; (C) 5 to about 50 weight % formic acid in acetonitrile; and (D) about 100% weight isopropanol; and combinations or mixtures thereof. In further embodiments, the mobile phase may be (A) about 0.01 to about 2 weight % trifluoroacetic acid in water, with increasing amounts over time of (B) about 0.01 to about 2 weight % trifluoroacetic acid in acetonitrile, followed by increasing amounts over time of (C) about 5 to about 50 weight % formic acid in acetonitrile. In still further embodiments, the mobile phase may be (A) about 0.01 to about 2 weight % trifluoroacetic acid in water with increasing amounts over time of (B) 0.01 to about 2 weight % trifluoroacetic acid in acetonitrile, followed by increasing amounts over time of (C) 5 to about 50 weight % formic acid in acetonitrile, and followed by increasing amounts over time of (D) 100% weight isopropanol.

In embodiments, fractionating a mixture of proteins on a reversed phase superficially porous stationary phase at elevated temperatures, and optionally with a multi-segment gradient elution as illustrated herein, provides, compared to a porous phase material, improved chromatographic performance such as enhanced peak selectivity, enhanced peak resolution, reduced band-broadening, and like improvements, or combinations thereof. For additional descriptions of chromatographic methods, performance, and terminology, see for example in: *HPLC of Biological Macromolecules, Methods and Applications*, Marcel Decker, Inc., vol. 51, 1990, chap. 1, and *Practical HPLC Method Development*, Snyder et al., 2nd Ed, John Wiley & Sons, Inc. 1997.

In embodiments, the mixture of proteins may be eluted, for example, with an elution gradient comprised of: from about 5 to about 30 weight % of from about 0.1 weight % aqueous trifluoroacetic acid in acetonitrile; from about 30 to about 55 weight % of from about 0.1 weight % aqueous trifluoroacetic acid in acetonitrile; from about 55 to about 100 weight % of from about 0.1 weight % aqueous trifluoroacetic acid in acetonitrile; and about 100 weight % of from about 0.1 weight % aqueous trifluoroacetic acid.

In yet other embodiements, the mixture of proteins may be eluted, for example, with a gradient comprised of: from about 5 to about 30 weight % of from about 0.1 weight % aqueous trifluoroacetic acid in acetonitrile for about 1 to about 10 min; from about 30 to about 55 weight % of from about 0.1 weight % aqueous trifluoroacetic acid in acetonitrile for about 5 to about 60 min.; from about 55 to about 100 weight % of from about 0.1 weight % aqueous trifluoroacetic acid in acetonitrile about 1 to about 20 min.; and about 100 weight % of from about 0.1 weight % aqueous trifluoroacetic acid for about 1 to about 20 min.

In another specific example, the mixture of proteins may be eluted, for example, with a gradient comprised of: from about 5 to about 30 weight % of 0.08 weight % aqueous trifluoroacetic acid in acetonitrile in 5 min; from about 30 to about 55 weight % of 0.08 weight % aqueous trifluoroacetic acid in acetonitrile in 33 min.; from about 55 to about weight 100% of 0.08 weight % aqueous trifluoroacetic acid in acetonitrile in 10 min.; and about 100 weight % of 0.08 weight % aqueous trifluoroacetic acid in 4 min.

In additional embodiments, a lipid-containing sample may be delipidated, for example, with an elution gradient comprised of:
about 80% weight percent (A) 0.01 to about 2 weight % trifluoroacetic acid in water and about 20 weight % of (B) about 0.01 to about 2 weight % trifluoroacetic acid in acetonitrile with addition over time of:
from about 20 to about 100 weight % of (B) about 0.01 to about 2 weight % trifluoroacetic acid in acetonitrile, in about 1 to 70 minutes;
from about 0 to about 100 weight % of (C) about 5 to about 50 weight % formic acid in acetonitrile, in about 1 to 20 minutes; and
from about 0 to 100 weight % of (D) about 100% weight isopropanol, in about 1 to 20 minutes.

In further embodiments, a lipid containing sample may be delipidated, for example, with an elution gradient comprised of:
about 80% weight percent (A) 0.01 to about 2 weight % trifluoroacetic acid in water and about 20 weight % of (B) about 0.01 to about 2 weight % trifluoroacetic acid in acetonitrile with addition over time of:
from about 20 to about 50 weight % of (B) about 0.01 to about 2 weight % trifluoroacetic acid in acetonitrile, in about 1 to 50 minutes;
from about 50 to about 100 weight % of (B) about 0.01 to about 2 weight % trifluoroacetic acid in acetonitrile, in about 1 to 20 minutes;
from about 0 to about 100 weight % of (C) about 5 to about 50 weight % formic acid in acetonitrile, in about 1-20 minutes; and
from about 0 to 100 weight % of (D) about 100% weight isopropanol, in about 1 to 20 minutes.

In further specific embodiments, a lipid-containing sample may be delipidated, for example, with an elution gradient comprised of:
about 80% weight percent of (A) 0.01 to about 2 weight % trifluoroacetic acid in water, and about 20 weight % of (B) about 0.01 to about 2 weight % trifluoroacetic acid in acetonitrile, with addition over time of:
from about 20 to about 50 weight % of (B) about 0.01 to about 2 weight % trifluoroacetic acid in acetonitrile in about 40 minutes;
from about 50 to about 100 weight % of (B) about 0.01 to about 2 weight % trifluoroacetic acid in acetonitrile in about 10 minutes;
from about 0 to about 100 weight % of (C) about 5 to about 50 weight % formic acid in acetonitrile in about 10 minutes; and
from about 0 to 100 weight % of (D) about 100% weight isopropanol, in about 5 minutes.

The methods of the present invention further provide methods for regenerating superficially porous solid phases described above. In one aspect, the solid phase may be used greater than about 5 times at temperatures of from about 40° C. to about 95° C., greater than about 10 times, greater than about 20 times, greater than about 30 times, greater than about 40 times, and greater than about 50 times. In certain aspects, after contacting the solid phase with the gradient compositions described above, the solid phase is contacted with a 100% organic phase, containing 0.08% trifluoroacetic acid. For example, in one aspect, the gradient is completed with 100% acetonitrile, containing 0.08% trifluoroacetic acid.

The load of proteins, such as a membrane or serum sample, on the solid phase may be, in embodiments, for example, from about 100 micrograms to about 2 grams, and preferably from about 100 micrograms to about 2,000 micrograms, and more preferably about 100 micrograms to about 200 micrograms.

The method may further comprise collecting each of the resulting separated or fractionated membrane sample lipids or proteins.

Reduction in Sample Complexity

As discussed above, in certain aspects, the complexity of the sample is reduced prior to contacting with a superficially porous phase. For example, the sample may be contacted with an affinity matrix for depleting a sample of undesired proteins, such as high abundance proteins. The nature of the protein to be removed will generally depend on the sample, and may include albumin, in the case of serum; phaseolin, zein, globulins, protamines and glutinins, in the case of certain plants. Other proteins which may be removed from a sample include, but are not limited to: oil seed proteins, Rubisco, ribosomal proteins, both chloroplast and cytosolic, thylacoit, photosynthesis system I proteins, photosynthesis system II proteins, chloroplast membrane binding proteins and other structural proteins, viral proteins, bacterial proteins, and the like.

The immunoaffinity phase, if selected for depletion in the method, may comprise for example, an affinity binding composition comprising: a first and second solid phase matrix comprising a first receptor immobilized on a first solid phase matrix, capable of specific binding to a first ligand but not a second ligand; and a second receptor immobilized on a second solid phase matrix, capable of specific binding to the second ligand but not the first ligand (e.g., under binding conditions to which the solid phase is exposed).

In certain aspects, the first and second sold phase matrix are mixed together in a column or in a solution. For example, the first and second solid phase matrix may contact each other. In certain other aspects, the first and second solid phase matrix do not form discrete zones as in a test strip. The solid phase may comprise additional receptor molecules, such as an optional third receptor immobilized on a third solid phase matrix, capable of specific binding to a third ligand but not the first ligand or the second ligand; an optional fourth receptor immobilized on a fourth solid phase matrix, capable of specific binding to a fourth ligand but not the first ligand, the second ligand or the third ligand; and an optional a fifth receptor immobilized on a fifth solid phase matrix, capable of specific binding to a fifth ligand but not the first ligand, the second ligand, the third ligand or the fourth ligand.

As used herein, a "receptor" may include any molecule that may serve as a binding partner for any molecule to be depleted from a sample. For example a receptor may comprise an antibody or antigenic fragment thereof. However, a "receptor" as used herein is not necessarily a protein, but may also comprise a polypeptide, peptide, metal, metal coordination compound, carbohydrate (e.g., a lectin, such as concanavalin A or wheat germ agglutinin), aptamer, nucleic acid, co-factor, heparin, polymyxin, dye (such as Cibacron blue F3GA), a hydrocarbon (such as a methyl and phenyl radical that binds hydrophobic proteins), an agent comprising a functional group with affinity for protein moieties (such as a hydrazide, amine, N-hydroxy-succinimide, carboxyl, boronate and organomercury molecule) and generally, or any other molecule with the desired binding specificity.

Immunoaffinity liquid chromatography stationary phases or solid phases are described, for example, in the above mentioned U.S. Published Patent Application No. 20040115725.

Immunoaffinity columns may also be used to enrich for desired proteins prior to delipiation. For example, a sample may be contacted with an immunoaffinity solid phase comprising at least a first receptor that is a binding partner for a protein (or type of protein) to be enriched for in the sample. The proteins bound to the immunoaffinity solid phase may be of interest for further separation by superficially porous phases according to the disclosure, rather than those proteins that are in the immunodepleted sample flowing past the immunoaffinity stationary phase. Thus, in one aspect, a sample may be contacted with an immunoaffinity stationary phase to provide complexes of proteins bound to the immunoaffinity stationary phase and the bound proteins are then eluted for further separation by the superficially porous phase.

As with the immunodepletion columns described above, immunoaffinity stationary phases for enriching protein samples may comprise a plurality of different binding molecules or receptors with different and exclusive affinities (e.g., binding to one ligand but not another) under the conditions being used. In one aspect, for example, an immunoaffinity stationary phase comprises a binding partner (such as an iodacetate derivative) for selecting cysteine-containing peptides. In another aspect, the immunoaffinity column comprises a binding partner for binding carbohydrate-comprising proteins and the like. In a further aspect, the immunoaffinity stationary phase binds both types of proteins. A receptor for enrichment of a sample may include, but is not limited to, an antibody or antigenic fragment thereof, a polypeptide, peptide, metal, metal coordination compound, carbohydrate (e.g., a lectin, such as concanavalin A or wheat germ agglutinin), aptamer, nucleic acid, co-factor, heparin, polymyxin, dye (such as Cibacron blue F3GA), a hydrocarbon (such as a methyl and phenyl radical that binds hydrophobic proteins), an agent comprising a functional group with affinity for protein moieties (such as a hydrazide, amine, N-hydroxy-succinimide, carboxyl, boronate and organomercury molecule) and generally, may comprise any molecule with the desired binding specificity.

In certain aspects, a sample is both immunodepleted to remove undesired proteins and immunoselected to enrich for desired proteins, prior to contacting with superficially porous phase according to the disclosure. In other aspects, a separation method described above may be combined with one or more additional separation methods. For example, the separation method may be combined with one or more of: gel filtration, liquid chromatography, ion exchange chromatography, electrophoresis (e.g., such as gel electrophoresis, capillary electrophoresis) and the like. Accordingly, phases according to the disclosure may be interfaced via fluidic couplings, e.g., columns, capillaries, microfluidic chips, combinations thereof, and the like, to devices for performing any of the above-mentioned separation techniques. Prior to analysis, and/or prior to separation and/or prior to affinity selection or immunodepletion, proteins may further be fragmented by a cleaving agent to generate peptides which may be analyzed and which may provide a signature for a protein from which it is derived, e.g., detection of the peptide may be diagnostic of the presence of the protein in a sample.

The method may further comprise analyzing at least one of the separated portions of lipids and proteins. For example, any of the separation methods described above may be combined with a method for proteomic analysis, such as two-dimensional gel electrophoresis, mass spectrometry (including, but not limited to MALDI-TOF-MS, ESI, TOF, ion trap mass spectrometry, ion trap/TOF mass spectrometry, quadropole mass spectrometry, Fourier Transform mass spectrometry, fast atomic bombardment (FAB), plasma desorption (PD), thermospray (TS), and magnetic sector mass spectrometry and the like), NMR and other techniques. The separated protein portion or lipid portion may be analyzed, collectively or individually, to identify protein(s) of interest.

Peptide sequence information may be automatically generated by selecting peptide ions of a particular mass-to-charge (m/z) ratio for collision-induced dissociation (CID) or other means for generating peptide ions known in the art. The resulting ionization spectra may then be correlated with sequences in sequence databases to identify the protein from which the sequenced peptide originated, e.g., using computer searching algorithms known in the art.

Peptides may be quantified by measuring the relative signal intensities for pairs of peptide ions of identical sequence that are tagged using different mass-altering labels, e.g., such as light or heavy forms of isotope, or which comprise label and unlabeled peptide pairs (which differ in mass by the mass of the label). In certain aspects, a peptide or mass-altering portion of a peptide may comprise a detectable label, such as a radioactive label, spin label, chemiluminescent label, and the like.

In one embodiment, methods according to the disclosure are used to evaluate samples which have been exposed to an agent, e.g., lipids and/or proteins from a sample exposed to an agent are separated using superficially porous phases under conditions described above and may be analyzed using proteomic analysis methods such as mass spectrometry. The fractioned proteins may be compared to proteins in a reference sample that comprise a sample which is not exposed to the agent. Additional samples may comprise samples exposed to different concentrations of agents. Suitable agents which may be evaluated include, but are not limited to: drugs; toxins; proteins; proteins; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers), and combinations thereof. Agents also may be obtained from synthetic libraries that are commercially available or generated through combinatorial synthesis using methods well known in the art.

Agents associated with a desired cell state or the transition from an undesired cell state (e.g., a pathology) to a desired cell state (e.g., absence of the pathology or reduction in symptoms or biomarkers diagnostic of the pathology) may be identified as candidate compounds for treating the undesired cell state, for example, in a patient from whom the sample of cells was derived. Such compounds may be formulated as pharmaceutical compositions using methods known in the art.

In certain aspects, expression of a protein-rich sample or set or proteins, and/or modified and/or cleaved forms thereof, including lipid-containing membrane-bound proteins, associated with a particular cell state may be used to generate diagnostic probes to detect or screen for the cell states. As used herein, "expression" refers to a level, form, or localization of product. For example, "expression of a protein," including lipid-containing membrane-bound proteins, refers to one or more of the level, form (e.g., presence, absence or quantity of modifications, or cleavage or other processed products), or localization of the protein. Such proteins (or modified or cleaved forms) may be detected directly, e.g., using mass spectrometry techniques or indirectly, e.g., using antibody probes.

In one embodiment, the disclosure further provides a system that interfaces superficially porous phases, according to the disclosure, with a lipid/protein analysis system, such as a mass spectrometer.

In one aspect, the system comprises a superficially porous phase provided in a column, capillary, or a channel (e.g., a microchannel or nanochannel) in a substrate. The superficially porous phase may itself be operably interfaced with an immunoaffinity phase, for example, provided upstream of the superficially porous phase in a column, capillary or channel format which operably interfaces with a column, capillary, or channel comprising the superficially porous phase by an appropriate fluidic connection (e.g., tubing, capillary, conduit, microfluidic system, and the like). As used herein, the term "operably interfaced" means that the interface is provided at an appropriate time such that fluid from an upstream column (e.g., an immunoaffinity support or stationary phase) may be provided to a downstream column (e.g., a separation column comprising superficially porous phase) at an appropriate time (e.g., to collect the flow through from an immunodepletion column or to collect eluted proteins previously bound to an immunoaffinity column which selects desired proteins).

In one aspect, a separation module (e.g., capillary, column, channel or the like) comprising superficially porous phases according to the disclosure interfaces with an mass spectrometer device through an interfacing module (such as an electrospray device, such as an electrospray capillary or nozzle) which delivers substantially purified lipids/proteins/peptides to the mass spectrometer. In the case where the analysis system comprises a MALDI device, an automated spotter may be used to connect a separation capillary to a MALDI device (see, e.g., Figeys et al., *Electrophoresis* 19:2338-2347 (1998).

Throughput of the delivery process may be increased using arrays of electrospray or nanospray needles. See e.g., Zubritsky et al., *Anal. Chem.* 72:22A (2000); Licklider et al., *Anal. Chem.* 72:367-375 (2000); Scherer et al., *Electrophoresis* 20:1508-1517 (1999).

In another aspect, the system comprises one or more detectors for detecting movements of fluids, proteins, and/or peptides through the system.

Generally, the mass spectrometer device of the system comprises an ionizer, an ion analyzer and a detector. Any ionizer that is capable of producing ionized peptides in the gas phase may be used, such as an ion spray mass spectrometer (Bruins et al., *Anal Chem.* 59: 2642-2647 (1987)), an electrospray mass spectrometer (Fenn et al., *Science* 246:64-71 (1989)), and laser desorption device (including matrix-assisted desorption ionization and surfaced enhanced desorption ionization devices). Any appropriate ion analyzer may be used as well, including, but not limited to, quadropole mass filters, ion-traps, magnetic sectors, time-of-flight, and Fourier Transform Ion Cyclotron Resonance (FTICR). In a preferred aspect, a tandem MS instrument such as a triple quadropole, ion-trap, quadropole-time-of flight, ion-trap-time of flight, or an FTICR is used to provide ion spectra. A FAB ionizer may also be used.

In another aspect, the system further comprises a system processor which may convert signals obtained from different components of the system (e.g., such as electrical signals) into data and may provide instructions for controlling one or more system functions. In one aspect, data includes, but is not limited to, data relating to binding conditions and/or elution conditions during affinity purification, data relating to separation, concentration, and/or purification of proteins/peptides eluted from a separation module comprising superficially porous phases, data relating to fluid movement in the system (e.g., the operation of pressure or electroosmotic pumps), as well as data relating to peptide fragmentation, ionization, peptide quantity and amino acid sequence.

In some aspects, the processor compares mass spectral data to sequences in a protein and/or nucleic acid sequence database which the processor may access remotely. Thus, in a further aspect, the system further comprises a memory for storing data relating to peptide masses, and/or amino acid sequence. In another aspect, the system additionally comprises an information management system for searching and comparing data in the memory and obtained from mass spectrometry analysis. However, in other aspects, the processor obtains sequence information directly from mass spectral data provided to it from the mass spectrometer. The type of protein or peptide analysis performed by the system processor will relate to the type of mass spectrometer or other protein analysis device used in the system.

In still another aspect, in response to data from various system components, the processor alters one or more functions of the system. In additional or alternative embodiments, the processor is programmed, for example, by a user of the system and/or remotely to provide particular system instructions.

The disclosure additionally provides computer program products comprising computer readable medium providing instructions to a processor in communication with a system described above to control one or more system functions, e.g., exposure of superficially porous phases to gradient compositions and/or temperature conditions, contacting proteins to a cleaving agent, ionization or peptide fragments, delivery of peptides to a mass spectrometer, analysis of mass spectra, and the like.

Useful reversed phase operational conditions have been developed using a herein described superficially porous column packing material that yields high recovery of the soluble proteins of human serum and plasma. See Martosella et al., *J. Proteome Res.* 4(5):1522-37 (2005) (herein incorporated by reference). As observed in this previous study, elevated column temperature operation is required to yield high protein recoveries, and to prevent rapid column fouling. Although these methods provided useful starting conditions, they were not sufficient for the reversed phase separation of membrane proteins. Indeed, specific sample treatment and mobile phases are needed to enable partial or full disassociation of protein from the membrane lipids, as well as for the regeneration of the RP surface by eluting strongly absorbed lipids and related materials.

Indeed, to be applicable for on-column delipidation, a reversed phase separation should resolve proteins effectively, tolerate the presence of residual detergents, complex lipids and other naturally-occurring biological materials. To be useful for proteomic analyses, the separation should also be both efficient and demonstrate reproducible lipid recoveries.

A robust multidimensional separation strategy for identifying membrane proteins are described herein, such that lipid raft proteins were simultaneously separated and delipidated, and resulting fractions were collected for downstream analysis by 1D gel electrophoresis and mass spectrometry. The mRP-C18 column, using herein-disclosed optimized chromatographic conditions, provided high protein recovery and excellent reproducibility. Thus, certain embodiments of the present invention are particularly suited for on-column dissociation of lipids from membrane proteins, giving researchers the benefit of improved protein fraction(s) purity and the opportunity to independently investigate the lipid fraction(s). Indeed, on-column delipidation, as described herein, results in resolved proteins with reduced lipid content and delayed elution of highly hydrophobic components occurring late in the separation. Thus, certain aspects of the present invention yield highly reproducible protein-lipid separations that are available for downstream SDS-PAGE, gel-free and/or mass spectrometry proteomic analyses.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

EXAMPLES

Materials Used: HPLC-grade acetonitrile and 2-propanol were purchased from VWR International (West Chester, Pa.). Formic acid (98-100%) was obtained from Sigma-Aldrich. The water used was Milli-Q grade (Millipore, Bedford, Mass.). Trifluoroacetic acid and trifluoroethanol were purchased from Sigma (St. Louis, Mo.). Sequencing grade-modified trypsin was from Promega (Madison, Wis.). Trypsin In-Gel Digestion Kit was from Agilent (Palo Alto, Calif.). The 50 ml conical BD polystyrene tubes were obtained from VWR International. Pre-cast gels were obtained from Invitrogen (Carlsbad, Calif.). The reversed phase column used in this study was a 4.6 mm×50 mm ID macroporous reversed phase C18 column from Agilent Technologies (Wilmington, Del.). The 5 peptide mixture used is the Alberta Peptide Institute Standard RPS-P0010 (API, Edmonton, AB).

Preparation of lipid raft-enriched fraction: The lipid raft-enriched fraction was prepared by detergent extraction on ice and flotation on a sucrose gradient. Frozen mouse brains (sectioned at the pons, with cerebellum removed, and hereafter referred to as cerebra; obtained from PelFreez, Rogers, Ark.), or neurologically normal human brain neocortex (Superior Temporal Gyrus, kindly supplied by Drs. T. Beach and D. G. Walker, Sun Health Research Institute, Sun City Ariz.) were employed for the preparation of membrane rafts. All steps were carried out on ice or at 4° C.

Pieces of frozen brain tissue (1.2 g) were homogenized on ice in 20 ml of cold TBS (10 mM Tris-HCl, 150 mM NaCl, 1 mM EDTA, pH 7.4) with Complete Protease Inhibitor Cocktail (Roche Diagnostics, Indianapolis, Ind.) using a Polytron homogenizer (Brinkmann, Westbury, N.Y.) (2 times for 10 sec). A chilled solution of 20 ml of 2% Triton X-100 in TBS buffer (final concentration was ~3 mg/ml in 1% Triton X-100) was added to the sample. The sample was mixed by inversion 5 times and incubated on ice for 30 min. After incubation the sample was adjusted to 40% sucrose by the addition of equal volume (40 ml) of 80% sucrose in TBS buffer. A discontinuous sucrose gradient was formed in the centrifuge tubes (Rotor JS-24.38, Beckman Coulter, Fulerton, Calif.). 12 ml of sample solution was placed on the top of 1.6 ml of 80% sucrose followed by 12 ml of 35% sucrose and 12 ml of 5% sucrose, all in the presence of TBS. The gradients were centrifuged for 42 hours at 103,900×g. During high speed centrifugation, lipid rafts migrated to the low-density region of the gradient due to their high lipid content. The low-density material floating at the 5-30% interface was collected, diluted 4 times in TBS and centrifuged for 2 hrs at 200,000×g to pellet the detergent-resistant fraction. The resulting pellet was resuspended in 2 ml of TBS and pelleted by centrifugation as above. One additional washing of the pellet was performed. Final pellets were dispersed in 2 ml of H2O, then stored at −80° C. until use.

Electrophoretic analysis: SDS-PAGE analysis was performed on Invitrogen Tris-glycine precast gels (4-20% acrylamide, 10 wells, 1 mm). Samples from reversed phase separations were dried in SpeedVac on low heat. Following resuspension in 2×sample preparation buffer, samples were heated for 1 min. at 50° C., and then loaded onto the gel. Gel-separated proteins were visualized by Coomassie Blue staining using Pierce GelCode Blue.

100 µl (500 µg protein) of membrane rafts were dried in a centrifugal vacuum concentrator (Thermo-Savant, Millford, Mass.), resolubilized in 200 µl of 80% formic acid (FA) and sonicated in a water bath for 30 seconds. The samples were dried in the centrifugal vacuum concentrator, resolubilized in 500 µl of 80% FA and sonicated in a water bath for approximately 30 seconds or until a clear mixture resulted. The final sample protein concentration was approximately 1 mg/ml in 80% FA.

HPLC Separation and Fraction Collection: HPLC separations were performed on an automated Agilent 1100 LC system with an autosampler equipped with a 900 µl capillary loop. All the RP separations for membrane rafts were performed at about 80° C. using a combined multi-segmented and linear elution gradient, with eluent A (0.1% TFA), eluent B (0.08% TFA in acetonitrile (ACN), v/v), eluent C (20% formic acid in ACN v/v) and eluent D (2-propanol). The gradient flow rate was 0.75 ml/min. and elution conditions consisted of two segments with increasing concentrations of eluent B:20-50% B in 40 min., 50-100% B in 10 min. and a hold of 100% B and two subsequent linear elutions with increasing and decreasing concentrations of eluent C:0-100% in 5 min., 100-0% in 5 min. and eluent D: 0-100% in 5 min., 100%-0% in 5 min. for a total runtime of about 80 min. For consecutive runs, a 30 min. post run comprised of 3 min. 100% eluent D, followed by 20% eluent B (80% eluent A) for column re-equilibration.

Lipid raft separations were monitored at 280 nm and fractions were automatically collected at 1-2 min. intervals. Each fraction was dried in a centrifugal vacuum concentrator (Thermo-Savant, Milford, Mass.) and stored at −80° C. for subsequent SDS-PAGE and LC-MS/MS analysis.

RP separations of the five peptide standard was performed using a linear elution gradient of eluent A (0.1% TFA) and eluent B (0.085% TFA in 80/20 ACN/water, v/v) with increasing eluent B from 3-20% in 30 min. at 0.75 ml/min. Chromatograms were monitored at 210 nm.

Protein Recovery: Lipid rafts were fractionated on a 4.6 mm ID×50 mm mRP-C18 column under the conditions described above. The eluent was collected and samples analyzed according to a procedure described for protein isolation by Martosella et al., J. Proteome Res. 4 (5):1522-37(2005). See also generally U.S. Publ. Patent Appl. 2006/0070954. Briefly, total column effluent was collected into 50 ml polystyrene conical tubes (VWR International). Control runs were performed in the same manner, however, with the column removed from the flow path. Control and column eluates (approx. 47 ml) were dried in a speed vacuum concentrator at medium drying temperatures overnight. Dried samples of column and control runs were solubilized with 0.5 ml of 6 M urea, 1% Triton X-100 and 0.25% acetic acid. Samples were vortexed extensively to solubilize all protein and remove any material adhering to the tube walls. Samples were transferred to Eppendorf tubes and sonicated in a water bath for approximately 2 minutes. Protein quantitation was performed by BCA protein assay (Pierce). 50 µl of sample was mixed with deionized H2O to a final volume of 100 µl and the protein assay performed according to manufacturer's suggested protocol.

Recovery results were also evaluated using the EZQ Protein Quantitation kit from Invitrogen/Molecular Probes (Carlsbad, Calif.). 1 µl of each sample was spotted onto assay paper and the samples were fixed, washed and stained with EZQ stain according to the manufacturer's protocol. Each sample was then processed in quadruplicate and fluorescence measured by scanning on a Typhoon 8600 laser scanner (Amersham Biosciences, Piscataway, N.J.) using a 532 nm laser for the excitation and the 580 nm emission filter.

Protein In-Gel Digestion and LC-MS/MS: A total of 48 gel bands were cut and digested with trypsin according to the instructions provided in the Trypsin In-Gel Digestion Kit. The digested peptides were extracted and proteins were identified by LC-MS/MS analysis (Agilent 1100 nano-LC and 1100 MSD trap XCT equipped with a nanoelectrospray ionization source). 70% of the total volume of extracted peptides from each gel band were loaded onto a Zorbax 300SB-C18 (3.5 µm, 0.075 mm ID.×150 mm) capillary column. Proteolytic peptide fragments were gradient eluted where Buffer A was 3.0% ACN and 0.1% FA, and Buffer B was 90% ACN and 0.1% FA. The gradient was 5-12% B in 5 min., 12-35% B in 35 min., 35-65% B in 10 min., 65-100% B in 5 min., followed by 5 min. 100% B and re-equilibration at 5% B, for a total run time of 62 min. The XCT ion trap mass spectrometer was operated in standard scan mode for MS analysis and in ultra scan mode for MS/MS.

Protein In-Solution Digestion and Chip-Based Nano-LC-MS/MS: Dried human lipid raft protein fractions were resolubilized, reduced, alkylated and then digested with trypsin according to previously published procedures. The peptide digests of each mRP-C18 fraction were analyzed with a microfluidic chip-based nano-LC-MS/MS system (Agilent Zorbax 300SB-C18, 5 µm, 0.075×0.043 mm HPLC chip, HPLC-Chip/MS system with 1100 ion trap XCT Ultra). The RP buffers were the same as those described above and the gradient was 5-10% B in 2 min., 10-35% B in 18 min, 35-50% B in 2 min., 50-95% B in 0.5 min., followed by one minute at 95% B and re-equilibration at 5% B, for a total run time of 26 min. The ion trap mass spectrometer was calibrated using a built-in automated calibration algorithm, with the tuning mix specifically designed for this type of instrument. MS/MS data were searched against the SwissProt Human database (total of 12015 entries), using Spectrum Mill computer database search algorithm, with the "Calculate Reversed Database Scores" option "on". The peptide/protein hits were filtered with the "autovalidation" option using the following parameters: minimum score for peptides: +1, 7.0; +2, 8.0 (if SPI larger than 90%, the score was lowered to 7.0); +3, 9.0; +4, 9.0. All peptide matches were required that "Forward-Reverse Score" is larger than 1.0, and "Rank 1-2 score" is larger than 1.0. The protein score was set at minimum of 15.0. Only fully tryptic peptides were considered, with two missed cleavages allowed.

Lipid Partitioning and MS Analysis: The final set of combined fractions from the mRP-C18 column, which eluted in ACN/FA and 2-propanol, was injected onto a model 1100 capillary LC/MSD quadrapole SL system (Agilent Technologies) using a 0.5 mm ID×150 mm Zorbax SB-C18 column, (3.5 µm, 300 Å), at room temperature. An injection volume of 5 µL was used. The mobile phase was 80% methanol/15% tetrahydrofuran/5% water (v/v/v) containing 0.1% FA at a flow rate of 12 µL/min. The MSD was operated using an ESI source with positive ion polarity. The nebulizer pressure was 30 psi, drying gas flow rate was 7 µl/min, drying gas temperature was 300° C., and the capillary voltage was 4000 V. The MSD was scanned over the range of 150-1200 m/z, while setting the fragmentor voltage to +100 or +400 V to obtain either molecular ion information or fragmentation information in alternate scans, respectively.

Sample Preparation Considerations for Lipid Raft Protein Separations: A major difficulty arises in preparing detergent resistant membrane raft preparations as dispersed solutions for injection on an LC system, as many sample components exhibit visible solubility problems. Initial work using membrane rafts derived from frozen mouse cerebra employed various combinations of chaotropes (urea up to 6 M, urea/thiourea mixtures), organic modifiers (hexafluoroisopropanol), trifluoroacetic acid, as well as 2% SDS. The efficiency of solubilization was determined by extraction, centrifugation, and BCA assay of soluble supernatants and where possible, SDS-PAGE analysis. For a typical experiment, crude membrane raft preparations contained approximately 0.94 µg/µl of protein. After pelleting and solubilization in test solutions of the same volume, concentrations ranged from, a minimum of 0.38 µg/µl using 2% SDS to a maximum of 1.67 µg/µl, using 80% FA. Other samples were found to have concentrations somewhere between these two extremes. During protein recovery analysis lipid raft samples solubilized in FA repeatedly resulted in higher protein concentrations when measured after the reversed phase separation as compared with the sample run without the column. This may be explained by RP column dissociation of tightly-bound lipid from proteins, causing a concomitant reduction in interference during the protein assay. This explanation is consistent with gel band intensities, when samples were examined by SDS-PAGE and stained with colloidal Coomassie Blue. SDS-PAGE analysis uniformly indicated much higher protein band intensities for the FA extracts, although proteins solubilized with 2% SDS gave the best protein separation on these gels (data not shown). Both extracts were observed to yield clear solutions, with no apparent flocculates or precipitate when centrifuged at 10,000×g. Due to the greatly improved recovery with 80% FA, as well as it's compatibility with RP-HPLC separation, this sample matrix was used for all subsequent work.

Separations Method Development: Previous work with serum protein separations employed elevated column temperature with a multi-segmented linear gradient of water (0.1%TFA) and ACN (0.1% TFA). Although initially promising for FA solubilized lipid raft proteins, repeated injections exhibited inconsistent peak shapes and excessive band broadening, both of which grew worse with increasing sample numbers. A likely explanation is that the high lipid and cholesterol content (50% or greater by mass), combined with highly hydrophobic membrane proteins, as well as residual Triton X-100 in the raft preparations, leads to irreversible coating of the surface of the column packing material. By analogy with approaches successfully used for 2D-PAGE sample preparations, acetone and ethanol delipidation procedures were attempted for both the crude lipid raft preparation, as well as the FA solubilized lipid rafts. HPLC of the resolubilized pellets after delipidation however, showed a loss of protein mass by SDS-PAGE, diminished UV absorbance by HPLC, as well as significant band broadening and elevated column back pressures. This suggests that delipidation was incomplete, protein components are lost during the procedures, and/or irreversible aggregation of proteins in the sample may occur during these sample cleanup procedures.

A RP approach has the benefit of reducing the loss of proteins in the sample and also minimizes sample handling processes. Since sample injections at elevated temperature using binary water/ACN gradient elution generate acceptable initial separations, with good recovery, subsequent method development was concerned with defining mobile phases more capable of an effective elution of strongly retained components, in a fully soluble form. For comparison of the utility of conditions, both lipid raft protein samples were employed, as well as synthetic peptide standards, to evaluate the regeneration of column packing surfaces by examining elution repeatability.

Previous reports have described the use of FA and 2-propanol as mobile phase components for membrane protein separations. Use of a quaternary system facilitated complete regeneration of the column packing material, with an elution program that includes a gradient segment of 0.08% TFA in ACN to 20% FA in ACN. Full regeneration of the separation system further required an additional gradient segment from the FA/ACN mixture to neat 2-propanol. Attempts to eliminate these latter two segments resulted in unstable separations of the lipid raft protein samples, with drift in retention and increasing band width as the sample numbers increased. Operation of the system at significantly below about 80° C. may resulted in immediate column failure due to sample precipitation on the column.

Figure 2:
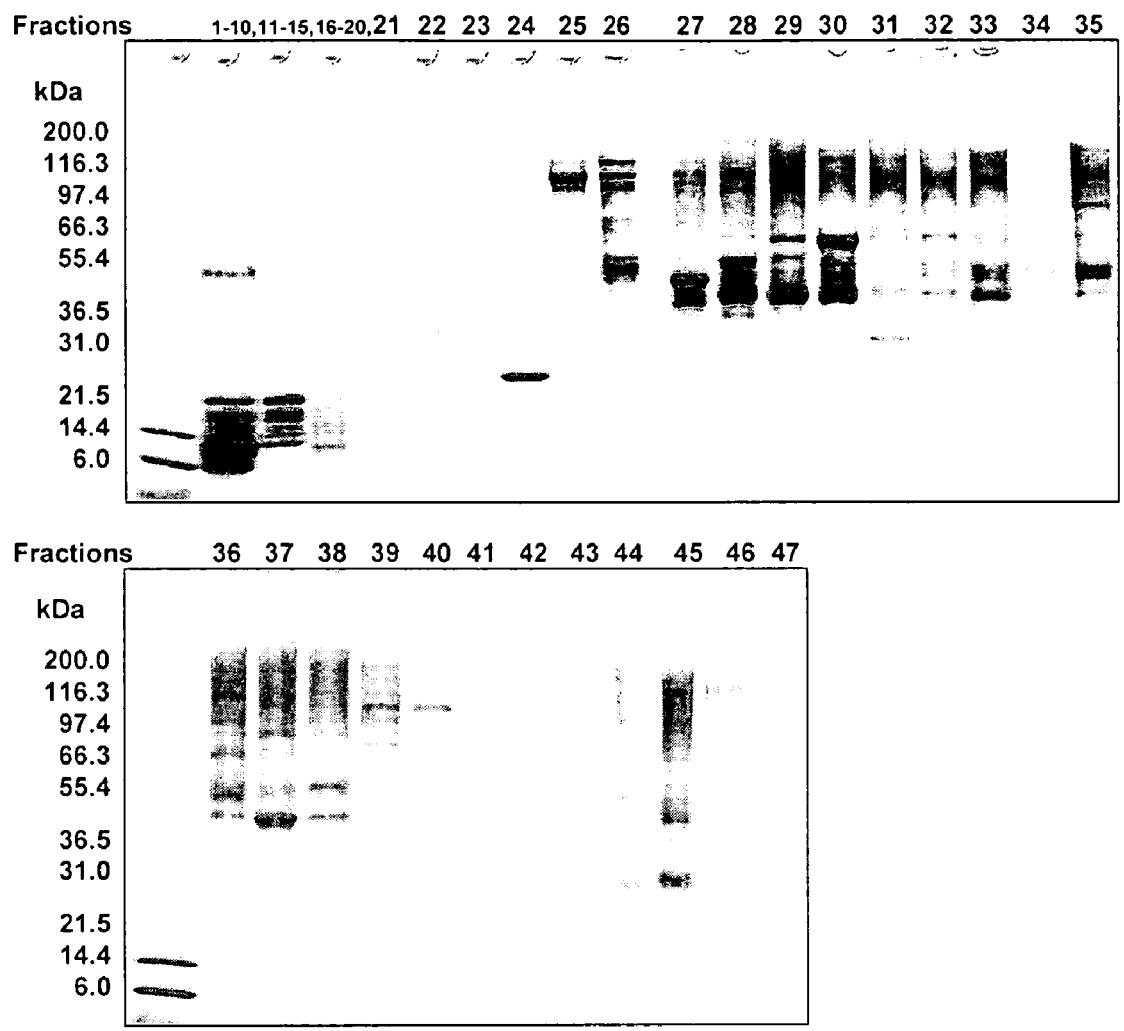
FIG. 2 depicts SDS-PAGE gel band patterns of the delipidated proteins at 1 minute fractions collected during the protein elution shown in FIG. 1.

The chromatogram in FIG. 1 shows the RP-HPLC separation of human brain membrane raft proteins using the conditions described above. In FIG. 2, SDS-PAGE analysis of column fractions was informative to define the properties of this separation. Examination of the gel band pattern on SDS-PAGE for the 1 minute fractions collected across this chromatogram shows that protein elution is completed by about 45-47 minutes, corresponding to 50-55% ACN. The separation may be described as exhibiting an early region in which essentially all of the proteins are eluted by increasing ACN, and a later region of eluting lipid material, driven by FA and 2-propanol, which is well away from the protein elution region. Systematic changes in the gradient composition to improve this separation, and further remove the lipid region, resulted in the preferred separation conditions detailed in the herein. The area extending from 48-70 min. contained a significant amount of lipids or lipid raft components which did not exhibit any significant quantity by protein assay or visible staining on SDS-PAGE analysis. This late eluting area of the separation was collected and further analyzed by ESI LC/MS as discussed below. Separation of the raft lipid components resulted from the combined ACN-FA/2-propanol reagent system and elevated temperature. On subsequent blank runs the chromatograms showed no evidence of peak ghosting or carryover.

Figure 3:
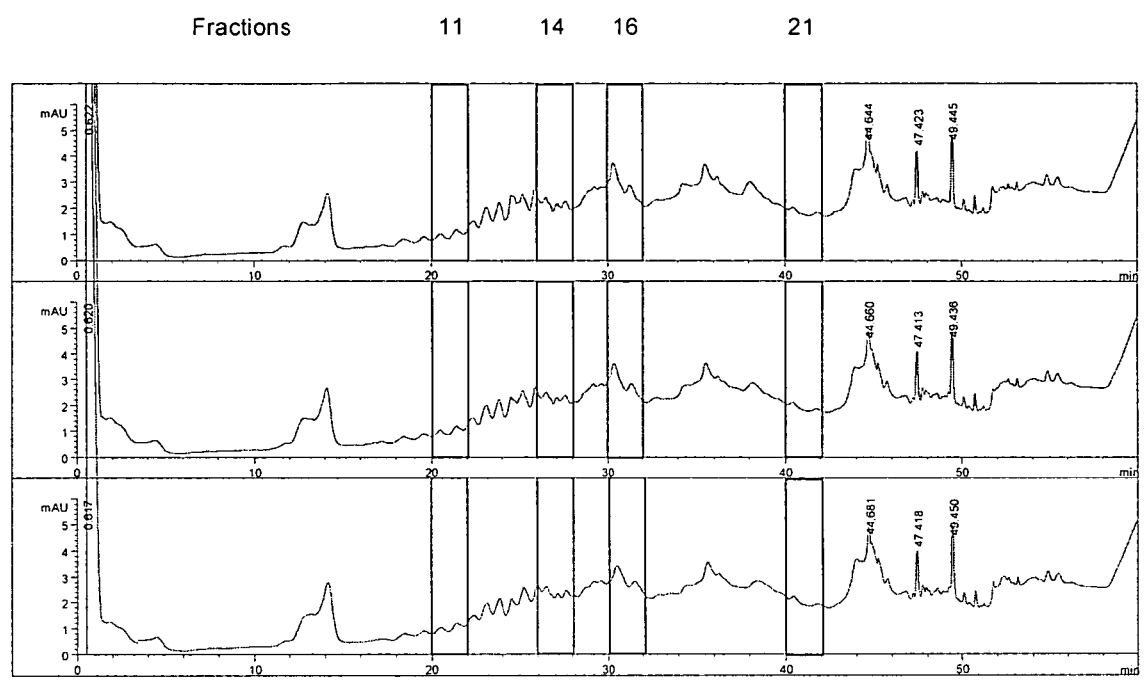
FIG. 3 shows an overlay of repeated separations exhibiting minimal changes from run to run in retention time, apparent selectivity, or band widths.

Chromatographic repeatability was examined using the preferred quaternary elution conditions and elevated temperature. Repeated separations of human membrane raft preparations for three injections were compared and are shown in FIG. 3. The RP separations are reproducible and show no changes from run to run in either retention times, apparent selectivity, or band widths. Blank runs performed after each separation are reproducible and show no indications of protein carryover or ghosting. Four fractions were selected from the separation, shown in FIG. 3, and evaluated protein identification repeatability by LC/MS/MS.

Proteins from the lipid rafts samples were RP fractionated three times under the same chromatographic conditions at 20, 26, 30 and 40 minutes (corresponding to fractions 11, 14, 16, and 21). Each fraction was digested in-solution with trypsin, and analyzed by a microfluidic chip-based nano-LC/MS system. For each time point, on average, more than 80% of the identified proteins in each individual run were shared by another run and more than 70% of the identified proteins were found in all three runs. The relatively high abundant proteins in each fraction (judging by the number of matched MS/MS spectra) were found in all three repeats. As used herein, "abundant sample proteins" comprise, for example, from about 50 to about 95 percent by weight of the total protein sample prior to depletion, and the mixture of proteins for fractionating may comprise, for example, less than about 50 percent by weight of the total protein prior to depleting. Such results are close to those obtained by repeat LC-MS analysis of the sample protein digests obtained by others. The MS signal intensities are very similar for this peptide as well as two others selected from this protein (data not shown). Comparisons of integrated ion intensities for each sample indicate similar recoveries of protein in the replicates, consistent with a repeatable RP separation. Both the protein ID results and individual peptide ion chromatograms displayed repeatable separations at the protein level.

Protein Recovery: High protein recovery is a critical parameter for useful protein pre-fractionation strategies, and elevated temperature plays an important role for achieving high recoveries. To test recovery of protein, a series of four injections of lipid raft preparations was conducted, with collection of the eluate. Starting protein concentrations were normalized against the control run (no column in the flow path). Optimized chromatographic separation provided high recovery of protein. Two methods of analysis (BCA and EZQ) yielded approximately 114% protein recovery from the column relative to the normalized injection. The modest increase in recovered protein results from the dissociation of lipids during the separation, with the effect that delipidated raft proteins are more accessible to the reactants of the protein assay.

Full regeneration of the separation system may only occur if all of the components of the injected sample are eluted during the separation. To evaluate the regeneration of the surface, separations of a mixture of synthetic peptide standards were conducted over the course of the use of a column for membrane raft protein separations. If hydrophobic proteins and/or lipids are irreversibly bound to the surface, unstable separations will likely result. A mixture of 5 peptides was used to monitor retention and selectivity after consecutive lipid raft injections. Peptide separations were compared for a new mRP-C18 column, and after 4 consecutive injections of 220 µg of membrane raft proteins. As shown in FIG. 3, no significant shift in retention, selectivity or bandwidth results from this challenge with the membrane protein sample. In both pre- and post-column injections, peptide peaks have retained nearly identical retention times. The same column was used extensively over several weeks, with no evidence of degradation of separation performance.

Column cleaning or regeneration methods with TFE have been proposed as a wash regime to remove irreversibly bound proteins. To investigate the possible adsorption of proteins during the separation, the column eluent was collected during a blank run (immediately after a lipid raft sample), as well as following an injection of 300 µl neat trifluoroethanol. These samples were dried, then analyzed by SDS-PAGE to detect proteins that may have been carried over between raft sample separations. The gel lanes from each method showed no evidence of protein (data not shown).

Mass Spectrometry: A total of 48 randomly cut gel bands were analyzed by nano-RP-LC/MS/MS using data dependent acquisition mode, and the resulting MS/MS spectra were analyzed with the Spectrum Mill database search algorithm. A total of 158 proteins were identified, from 940 unique peptides and 5945 matched MS/MS spectra. More than 85% of the proteins were identified with two or more unique peptides. The protein list was uploaded into GOMiner™ to analyze their biological functions and cellular localizations. The identified proteins were also manually examined by reference to the primary literature, as available, to assess the accuracy of localization in the appropriate subcellular compartment. The majority of these proteins returned with their predicted/known molecular functions and cellular localizations, 151 and 149, respectively. 73 proteins were identified as membrane proteins and 35 as integral membrane proteins (FIG. 4). Moreover, a large number of proteins were associated with the cytoskeleton (36) and mitochondrion (37). Overall, there were 103 proteins that were associated with intracellular organelles. The following are the major protein categories, according to their biological functions: protein binding, 63, transporter, 43 and hydrolase, 31.

Figure 5A:
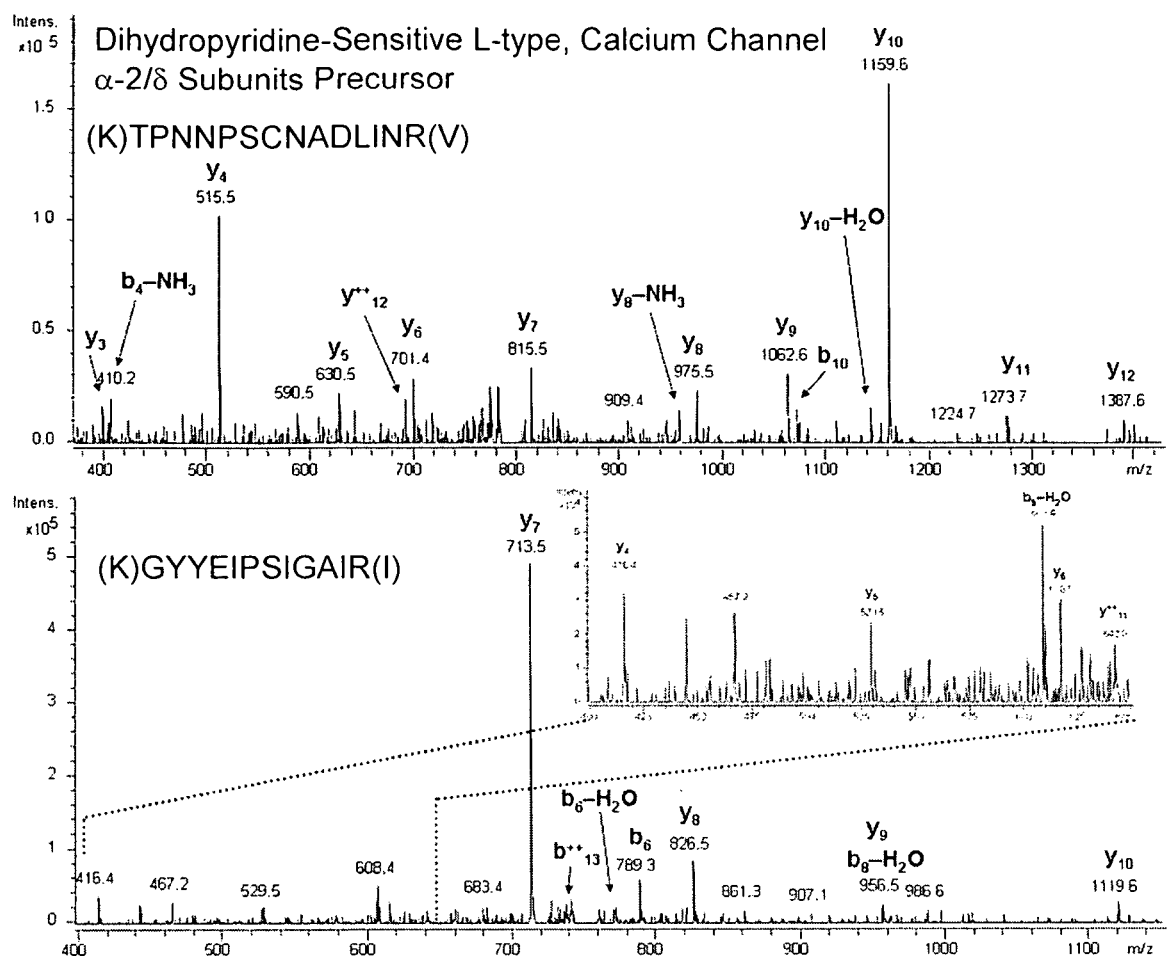
FIGS. 5A-5C each depict manual confirmation of MS/MS spectra.
Figure 5B:
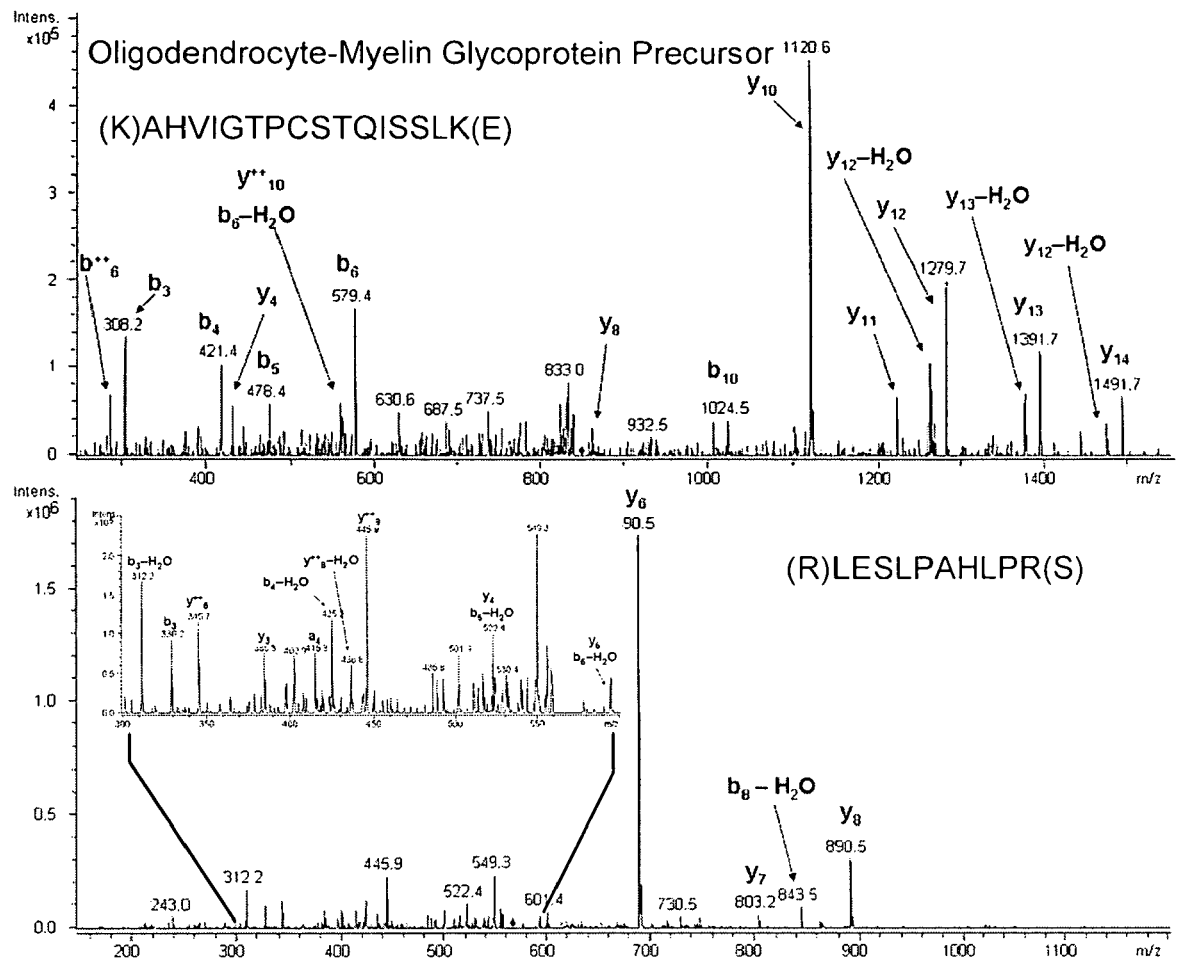
Figure 5C:
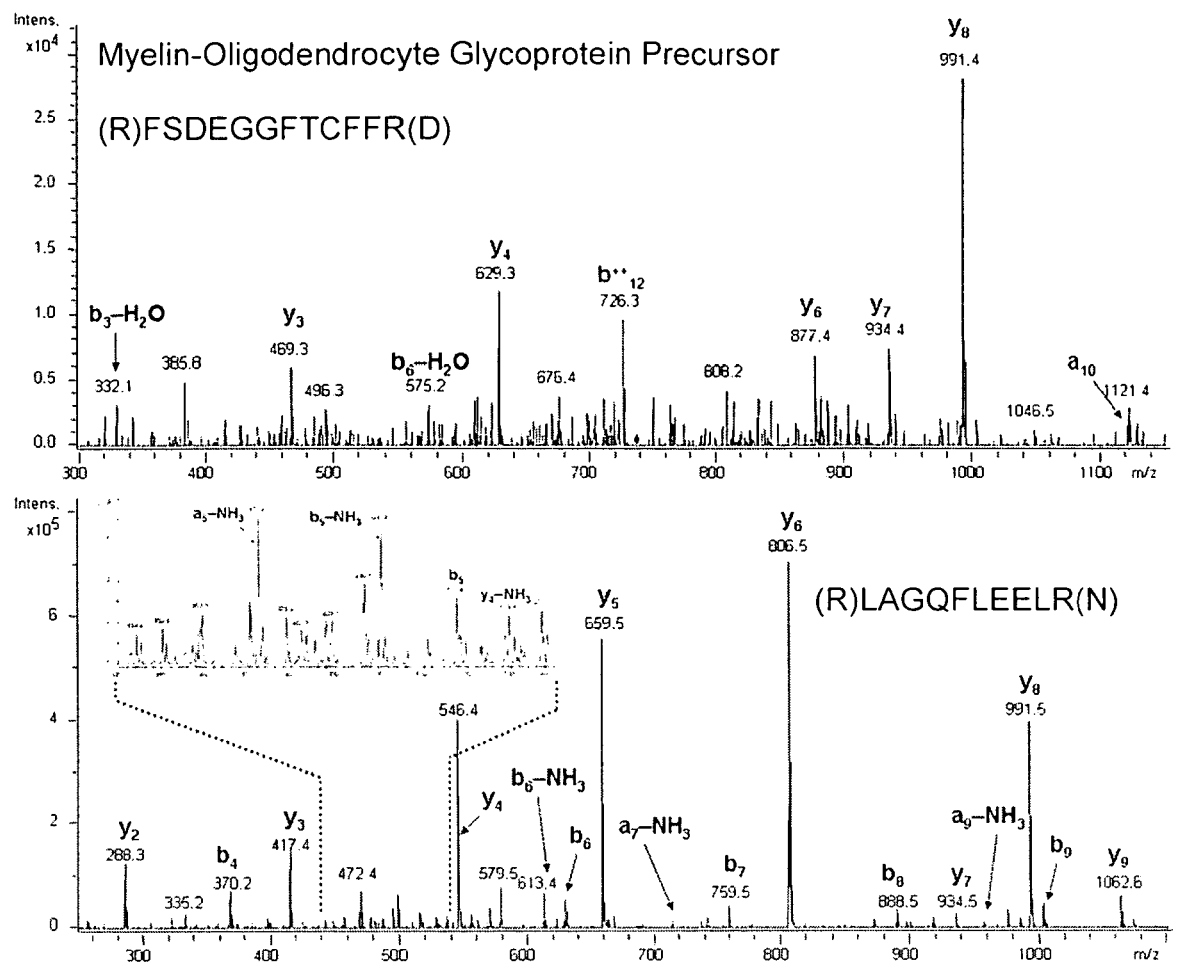

Many of the membrane proteins identified in this study had low protein identification scores, due to the relatively low numbers of spectra obtained and peptides identified for these proteins. In order to confirm these membrane protein identifications, the MS/MS data for these proteins were manually verified. FIGS. 5A-5C shows examples of three of these identified membrane proteins, where sequences of two of the detected peptide MS/MS spectra were used to manually confirm the identification of the proteins. For example, the spectra in FIG. 5B were used to confirm the identification of the 440 amino acid residue Oligodendrocyte-Myelin Glycoprotein Precursor protein, which is a cell adhesion molecule attached to the cell membrane via a GPI-anchor, and contributes to myelination in the central nervous system. The two peptides shown in these MS/MS spectra correspond to residues 247-262 (AHVIGTPLSTQISSLK), which is located within a Ser/Thr-rich domain, and residues 90-99 (LESLPAHLPR), which is found within a leucine-rich repeat region.

Figure 6:
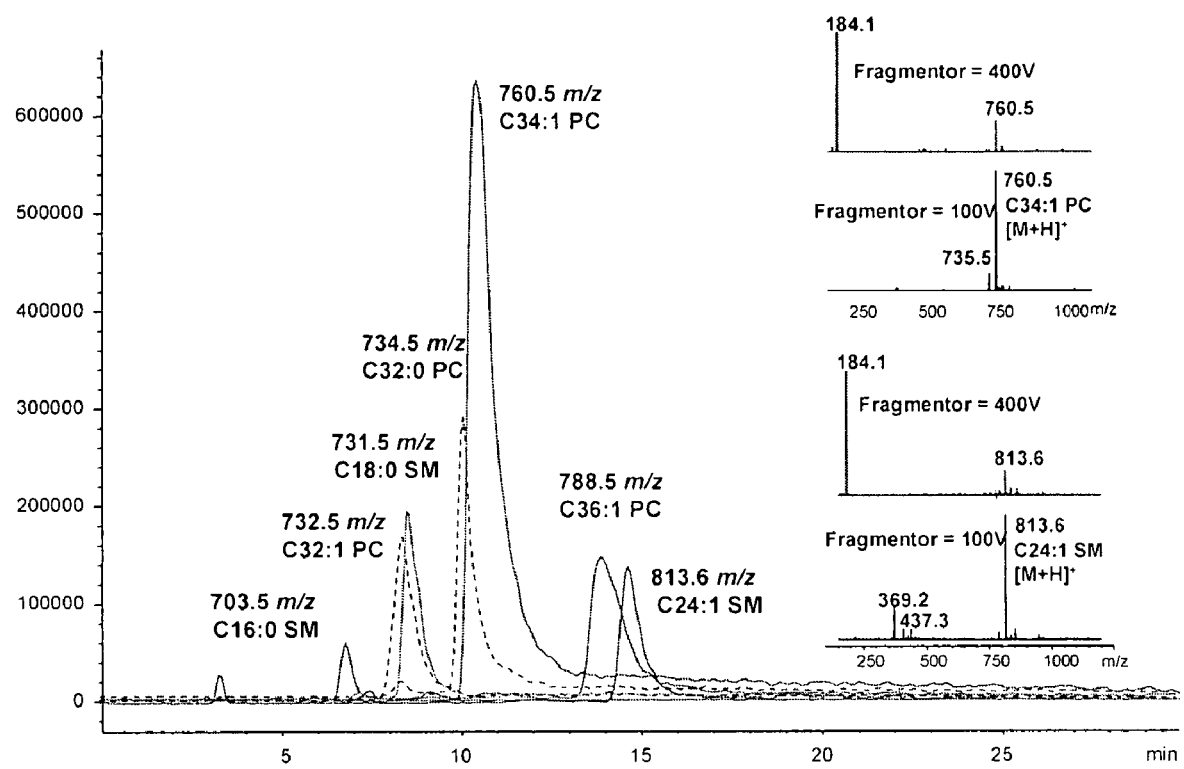
FIG. 6 shows the EIC's obtained at a fragmentor voltage of +100V.

MS identification of phospholipids in late-eluting column fractions: Late eluting column fractions collected after 47 min. were analyzed by LC/MS in order to generally confirm the presence of lipids. Phosphatidylcholines (PC) and sphingomyelins (SM) are significant constituents of the human brain. When analyzed by LC/MS in acidic media in the absence of alkali ions, they undergo loss of the charged phosphocholine head group under CID conditions to yield an ion at 184 m/z. This information, combined with the knowledge of the molecular ion, was used for identification. FIG. 6 shows the EIC's obtained at a fragmentor voltage of +100V; molecular ions corresponding to several species of PC and SM were detected. Under in-source CID conditions using a fragmentor voltage of +400V, these species yielded an intense ion at 184 m/z, confirming the presence of the phosphocholine head group.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

The invention claimed is:

1. An on-column delipidation method comprising separating a lipid-containing sample on a chromatographic column having at least one silica-based stationary phase, at a temperature of at least about 70° C.; wherein separation further comprises at least one mobile phase having an alcohol and at least one of the following eluents:
   (a) about 0.1 weight % of an ion-pairing agent in water;
   (b) about 0.08 weight %, of an ion-pairing agent in organic modifier; or
   (c) about 20 weight % of an acid in an organic modifier, or combinations thereof.

2. The delipidation method of claim 1, wherein at least one of:
   eluent (c) is varied from about 0 to about 100 weight % in about 5 minutes; and
   the alcohol is varied from about 0 to 100 weight % in about 5 minutes.

3. The method of claim 1, wherein the temperature is greater than about 80° C.

4. The method of claim 1, wherein the ion-pairing agent comprises at least one of trifluoroacetic acid (TFA), pentafluoroproprionic acid (PFPA), and heptafluorobutyric acid (HFBA).

5. The method of claim 1, wherein the ion-pairing agent comprises at least one of tetramethylammonium chloride, tetrabutylammonium chloride, and triethylamine.

6. The method of claim 1, wherein the organic modifier comprises at least one of acetonitrile, tetrahydrofuran (THF), methylene chloride, ethanol, methanol, ethanol, n-propanol, isopropanol, or combinations thereof.

7. The method of claim 1, wherein the sample is eluted with a gradient comprising increasing amounts of trifluoroacetic acid in at least one organic modifier, and variable concentrations of an acid in an organic modifier, and variable concentrations of an alcohol.

8. The method of claim 7, wherein the organic modifier comprises acetonitrile.

9. The method of claim 7, wherein the alcohol comprises isopropanol.

10. The method of claim 1, wherein the silica-based stationary phase is at least partially superficially porous.

11. The method of claim 10, wherein chromatography is performed by reversed phase-HPLC.

12. The method of claim 11, wherein the eluate is detected upon elution from at least one reversed phase-HPLC column.

13. The method of claim 12, wherein the sample, prior to separation, is solubilized in a solution comprising a strong acid.

14. The method according to claim 13, wherein said acid is formic acid.

15. The method of claim 11, wherein the sample load on the stationary phase comprises from about 100 micrograms to about 2 grams.

16. The method according to claim 11, wherein the superficially porous stationary phase comprises an average particle diameter of about 2 to about 20 micrometers.

17. The method according to claim 11, wherein the reversed phase comprises $C_6$ to about $C_{30}$ hydrocarbon selected from the group consisting of alkane, substituted alkane, alkene, substituted alkene, aryl or substituted aryl, and combinations thereof.

18. The method according to claim 11, wherein the reversed phase comprises a silane compound having at least one $C_{10}$ to about $C_{30}$ hydrocarbon.

19. The method according to claim 11, wherein the reversed phase comprises at least one divalent silane having a structure:

—Si(R)(Me)-(CH$_2$)$_3$—Si(R)(Me)- wherein R is n-octadecyl group, n-tetradecyl group, or mixtures thereof, and Me is methyl.

20. The method according to claim 11, wherein the reversed phase comprises at least one silane of the formula:

A—O—SiR$_1$R$_2$R$_3$ where $R_1$, $R_2$, and $R_3$ are each independently alkane, substituted alkane, alkene, substituted alkene, aryl or substituted aryl; and A is a surface group of the substrate to which the silane is attached.

21. An on-column delipidation method comprising separating a lipid-containing sample on a chromatographic column having at least one superficially porous stationary phase, at a temperature of at least about 70° C.; wherein separation further comprises at least one mobile phase having at least one of:

(a) about 0.1 weight % trifluoroacetic acid in water,
(b) about 0.08 weight % trifluoroacetic acid in acetonitrile,
(c) about 20 weight % formic acid in an organic acetonitrile, or
(d) isopropanol, or combinations thereof.

22. The delipidation method of claim 21, wherein at least one of:

eluent (a) is varied from about 20 to about 50 weight % in about 40 minutes;
eluent (b) is varied from about 50 to about 100 weight % in about 10 minutes;
eluent (c) if varied from about 0 to about 100 weight % in about 5 minutes; and
eluent (d) is varied from about 0 to 100 weight % in about 5 minutes.

23. The method of claim 21, wherein the temperature is greater than about 80° C.

24. The method of claim 21, wherein the chromatography is performed by reversed phase-HPLC.

25. The method of claim 21, wherein the eluate is detected upon elution from at least one reversed phase-HPLC column.

* * * * *

UNITED STATES PATENT AND TRADEMARK OFFICE
CERTIFICATE OF CORRECTION

| | | |
|---|---|---|
| PATENT NO. | : 7,943,046 B2 | Page 1 of 1 |
| APPLICATION NO. | : 11/472725 | |
| DATED | : May 17, 2011 | |
| INVENTOR(S) | : James D. Martosella et al. | |

It is certified that error appears in the above-identified patent and that said Letters Patent is hereby corrected as shown below:

On the title page, item (57), under "Abstract", in column 2, line 9, delete "aventageously" and insert -- advantageously --, therefor.

In column 1, line 7, delete "2006" and insert -- 2006, --, therefor.

In column 1, line 9, delete "2005" and insert -- 2005, --, therefor.

In column 26, lines 30-31, in Claim 4, delete "pentafluoroproprionic" and insert -- pentafluoropropionic --, therefor.

Signed and Sealed this
Twentieth Day of September, 2011

David J. Kappos
*Director of the United States Patent and Trademark Office*